US010872079B1

(12) United States Patent
Shiloh

(10) Patent No.: US 10,872,079 B1
(45) Date of Patent: *Dec. 22, 2020

(54) METHOD, SYSTEM, AND PREDICTIVE COMPUTING PLATFORM FOR GENERATING A REDUCED PATIENT-SPECIFIC DATA SUBSET OF DRUG-RELATED ADVERSE REACTION ALERTS

(71) Applicant: Seegnal eHealth Ltd., Savyon (IL)

(72) Inventor: Ron Zeev Shiloh, Mishmar Hashiva (IL)

(73) Assignee: SEEGNAL EHEALTH LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/794,299

(22) Filed: Feb. 19, 2020

Related U.S. Application Data

(63) Continuation of application No. 16/530,035, filed on Aug. 2, 2019, now Pat. No. 10,592,501, which is a continuation of application No. 14/000,976, filed as application No. PCT/US2012/028215 on Mar. 8, 2012, now Pat. No. 10,387,406.

(60) Provisional application No. 61/451,544, filed on Mar. 10, 2011.

(51) Int. Cl.
| | |
|---|---|
| *G06F 16/24* | (2019.01) |
| *G16H 20/10* | (2018.01) |
| *G16H 10/60* | (2018.01) |

(52) U.S. Cl.
CPC ............ *G06F 16/24* (2019.01); *G16H 10/60* (2018.01); *G16H 20/10* (2018.01)

(58) Field of Classification Search
CPC ..... G06F 16/24; G06F 19/3456; G16H 20/10; G16H 10/60
See application file for complete search history.

(56) References Cited

U.S. PATENT DOCUMENTS

| | | | | |
|---|---|---|---|---|
| 2002/0002473 | A1* | 1/2002 | Schrier | ................ G16H 70/40 705/3 |
| 2010/0070304 | A1* | 3/2010 | Levinson | .............. G06F 19/326 705/3 |

* cited by examiner

*Primary Examiner* — Linh Giang Le
(74) *Attorney, Agent, or Firm* — Greenberg Traurig, LLP

(57) ABSTRACT

A platform accessible by a user from a web browser/HMO's electronic medical record (EMR) for providing the user with information regarding a patient's drug regimen as well as generating alerts concerning potential adverse effects to a patient from taking a cluster including a plurality of pharmaceutical preparations and various food supplementals/herbals may be in data communication with and configured to obtain information from at least two databases and at least one tool for processing the cluster of pharmaceutical preparations in accordance with the information to generate the alerts to the user.

10 Claims, 16 Drawing Sheets

FIG. 2 (PRIOR ART)

Screen Sample of FDB Demo System

FDB Site: http://www.firstdatabank.com/Products.aspx

FIRSTDATABANK
DRUG INFORMATION FRAMEWORK US Version 3.3

Name: First [  ] MI [  ] Last [  ]
DOB: 1/1/1960  Gender: Female
Weight: [  ] kgs  Height: [  ] cms

Current Medical Profile

| Drug Name | Status | SiG |
|---|---|---|
| ⊗ Paroxetine 20 mg Tab | Current | |
| ⊗ Selegiline 5 mg Tab | Current | |

[Add] [Remove] [Alerts] [Explore] [AHFS Ref]

| Allergen | Reaction | Severity |
|---|---|---|

[Add] [Remove] [Alerts]

| Medical Condition | | Entry Date |
|---|---|---|

[Add] [Remove] [Alerts]

Prescribe | Dispense

● Retrospective Alerts
  └─ Drug Interaction Alerts
       └─ ⊗ SEROTONIN REUPTAKE INHIBITORS; SNRIS /S;
            ├─ Paroxetine 20 mg Tab
            └─ Selegiline 5 mg Tab Paroxetine 20 mg Tab and Selegiline 5 mg Tab may interact based on the potential interaction between SEROTONIN REUPTAKE INHIBITORS; SNRIS and SELECTED MAOIS (Contraindicated Drug Combination)

FIG. 3 (PRIOR ART)

HealthCare Burden (HCB) Estimator
HCB Alerts Matrix per Patient's Cluster

| Alert/Severity | FDB Data source | | | | | Genelex Data Source | | | | |
|---|---|---|---|---|---|---|---|---|---|---|
| | CI | SEVERE | MODERATE | MILD | Minor | >25% | >50% | >100% | <25% | >50% |
| Patient1 Cluster1 (Number of Alerts per Type Per each Cluster of a Patient) | 3 | 1 | 3 | 4 | 3 | 5 | 2 | 3 | 2 | 4 |
| Cluster2 | 1 | 1 | 1 | 2 | 2 | 0 | | | | |
| Cluster3 | | | | | | | | | | |
| ... | | | | | | | | | | |
| Patient N Cluster1 | 4 | 1 | 3 | | | | | | | |
| Cluster2 | | | | | | | | | | |

FIG. 12

Alerts details (Example)

| Drug Name | Alert Description (Actual Value) | Causative Agents | Owner | Link to Drill |
|---|---|---|---|---|
| HCB | | | | |
| HCB | Health Care Burden is High | Carbamazepine (50%), Selegiline (20%) | HMO | Ref. - Link |
| Paroxetine | | | | |
| Paroxetine | Synergistic Side Effects (Bleeding), Very Common) | Carbamazepine | User | Ref. - Link |
| Simvastatin | | | | |
| Simvastatin | Increased Serum Level Deviation > 50% (75%) | Carbamazepine, Clozapine | HMO | Link to SLD of Simvastatin |
| Carbamazepine | | | | |
| Carbamazepine | Contraindicated | Selegiline | HMO | Link to DI of Carbamazepine |
| Carbamazepine | Drug Interaction is Moderate - Severe (Severe) | Clozapine | HMO | Link to DI of Carbamazepine |
| Carbamazepine | Synergistic Side Effects (Bleeding, Very Common) | Paroxetine | User | Ref. - Link |
| Carbamazepine | Health Care Burden is High | Carbamazepine (50%), Selegiline (20%) | HMO | Ref. - Link |
| Clozapine | | | | |
| Clozapine | Decreased Serum Level Deviation < 50% (25%) | Carbamazepine | HMO | Link to SLD of Clozapine |
| Selegiline | | | | |
| Selegiline | Contraindicated | Carbamazepine | HMO | Link to SLD of Selegiline |
| Selegiline | Health Care Burden is High | Carbamazepine, (50%), Selegiline (20%) | HMO | Ref. |

FIG.14

METHOD, SYSTEM, AND PREDICTIVE COMPUTING PLATFORM FOR GENERATING A REDUCED PATIENT-SPECIFIC DATA SUBSET OF DRUG-RELATED ADVERSE REACTION ALERTS

PRIORITY INFORMATION

The present application is a continuation of U.S. patent application Ser. No. 16/530,035 filed Aug. 2, 2019, which is a continuation of U.S. patent application Ser. No. 14/000,976 filed Nov. 6, 2013, which is 371 national phase application of International Application No. PCT/US2012/028215 filed Mar. 8, 2012, which claims the benefit of U.S. Provisional Application No. 61/451,544 filed Mar. 10, 2011, the entire contents and disclosures of which are hereby incorporated by reference.

CROSS REFERENCE TO RELATED APPLICATIONS

This patent application claims the benefit of U.S. Provisional Patent Application No. 61/451,544 filed Mar. 10, 2011, the disclosure of which provisional application are herein incorporated by reference.

FIELD OF INVENTION

The present invention is directed to providing improved health care. Specifically, but not exclusively, embodiments of the invention are directed to a system and method for increasing patient's well-being at reduced cost.

BACKGROUND

Traditionally, western medicine is based on pharmacology. Drugs are selected to treat illnesses and diseases. Where an illness is chronic, the drugs treat the symptoms, and enable the patient to live as normal a life as possible.

In many cases, the patient requires treatment for a number of conditions. Indeed, this phenomenon is largely a sign of the success of western medicine, since patients are able to live a productive life despite having medical conditions that in an earlier period would have been dehabilitating if not fatal. Thus, aging patients in particular often require medicinal treatment involving a large number of drugs for multiple disorders. Sometimes this includes taking medicines to treat side-effects of other drugs prescribed. This phenomenon is sometimes referred to herein as poly-pharmacy.

There are a number of studies that have looked at unwarranted drug-drug interactions (e.g., adverse side effects, toxicity, and lack of efficacy) associated with combinations of various drugs on different populations. The amount of empirical material available is enormous, but various databases and computer programs exist to help physicians access the relevant information available and to use it in prescribing appropriate treatments to the individual patient. There are also various tools available that emulate the effect of drug interactions, such as the effect of one or more effector drugs on serum levels of concomitant drugs prescribed with the effector drug. Such tools may provide an indication of potential deviations of drugs from their expected serum levels, and aid in adjusting dosages.

Furthermore and due to their individual genetic profiles, various patients often metabolize drugs to different extents resulting in increases or decreases of the drug-serum levels in such patients. For example, some patients have a specific genetic profile that has been referred to as the "CYP2D6 poor metabolizer." Such patients have low-activity of a metabolic enzyme that is responsible for metabolizing specific drugs including antidepressant drugs such as Citalopram, duloxetine and maprotiline. Such a patient prescribed such an antidepressant may be subject to much increased serum levels of the drug, which can cause unwarranted adverse side effects, toxicity, lack of efficacy and the like.

A number of databases have been created and software has been developed to aid in prescribing an appropriate drug regimen for a patient.

By way of example, the GENELEX™ Database provides a commercially available database that calculates the potential effects of various drug-drug interactions on blood serum levels for different patient profiles. This information may be used to optimize drug prescription.

Since 2000, GENELEX™ has offered an alternative to the "one size fits all" and "trial and error" prescribing of drugs. In Genelex' perspective, Adverse Drug Reactions are not medical errors, but events that occur in spite of compliance with dosage recommendations. A 1998 meta-analysis of thirty-nine prospective studies in U.S. hospitals estimated that 106,000 Americans die annually from adverse drug reactions. Adverse drug events are also common (50 per 1000 person years) among ambulatory patients, particularly the elderly on multiple medications. The 38% of events classified as serious are also the most preventable.

FIRST DATABANK™ provides databases that mainly detail the clinical outcomes of drug-drug interactions and provide drug monographs.

International Patent Application Publication Number WO/05038049A2, entitled "System and Method for Optimizing Drug Therapy," relates to determining the dosage regimen for drug/pro-drug for the individual, and involves determining the metabolic profile of the individual and calculating individualized dosages of drugs according to a pharmacokinetic model.

Systems and the use of genotyping in the individualization of therapy and/or individualization of drug dosing are provided. More specifically, a pharmacokinetic model is described for the individualization of drug therapy.

Drug-drug interactions, gene-drug interactions, side-effects, non-responsiveness and toxicity are all discussed therein to some extent. The interaction of more than two drugs is referenced in passing. The system relates to clinical data, to the differences between different ethnic populations and to how the drugs are metabolized. The system described is supported on the web and has a graphic user interface designed to make accessing atypical events easy.

International Patent Application Publication Number WO/02086663A2, entitled "Computer System for Providing Information about the Risk of an Atypical Clinical Event Based Upon Genetic Information," describes a system for determining if a gene is associated with the atypical information.

Specifically, a computer system and method for preventing atypical clinical events related to information identified by DNA testing a person is described. The method includes receiving clinical agent information. The method also relates to determining if a gene is associated with the clinical agent information, and, if so, obtaining a genetic test result value for the associated gene of the person. The method further includes comparing the genetic test result value to a list of polymorphism values associated with an atypical clinical event, and determining whether the genetic test result value correlates to a polymorphism value on the list, and if so, outputting information about the atypical clinical event associated with the polymorphism value.

Drug-drug interactions, genetics, efficacy and toxicity are discussed. Personalized dosage and prescription are described. The system described therein includes a user friendly Graphic User Interface. Warning alerts are issued where a prescribed drug is likely to result in adverse effects.

U.S. Pat. No. 7,716,065, entitled "Method of Generating and Maintaining a Patient Medication Profile," describes a medical information processing method for providing detailed medication information that involves obtaining medication specific data, where the medication name and physical condition are obtained from sources independent of the patient.

The publication describes methods for conveniently providing a medication profile of a patient. A medication profile report may be obtained on-line by the patient or by a registered provider. In addition to information regarding the expiration of prescriptions, the patient's compliance with the prescriber's directions for usage, and the names of medications being used by a patient, the medication profile report also provides the therapeutic classes of each medication, possible drug-drug interactions, and possible side effects.

European Patent Application Publication Number EP01936525A1, entitled "Integrated Health Management Platform," describes a healthcare management method for a consumer, such as an employee of a company, which includes identifying the target of opportunity for the consumer according to the determined health-trajectory prediction from the multi-dimensional input data.

Apparatuses, computer media, and methods for supporting health needs of a consumer by processing input data are described. An integrated health management platform supports the management of healthcare by obtaining multi-dimensional input data for a consumer, determining a health-trajectory predictor from the multi-dimensional input data, identifying a target of opportunity for the consumer in accordance with the health-trajectory predictor, and offering the target of opportunity for the consumer. Multi-dimensional input data may include claim data, consumer behavior marketing data, self-reported data, and biometric data. A consumer may be assigned to a cluster based on the multi-dimensional input data and a characteristic of the consumer may be inferred. A cluster may be associated with a disease progression, and a target of opportunity is determined from the cluster and the disease progression. An impact of the target of opportunity may be assessed by delivering treatment to a consumer at an appropriate time. The system uses clinical medical data, published data from journals and metabolic biometric data from monitors attached to patients.

The web based system combines information from a health maintenance organization, and is a leaning platform that incorporates a physician's comments, creates rules and validates them. It uses a consumer profile and lifestyle and health behavior to present information via an intuitive Graphic User Interface.

International Patent Application Publication Number WO/02089017, entitled "A Method and System for Web-Based Analysis of Drug Adverse Effects," pertains to a computer-implemented method for assessing and analyzing the risks of adverse effects resulting from the use of at least one drug of interest for storing data regarding the risks of adverse effects from the use of at least one drug of interest in one or more servers linked to the Internet; updating such data regarding the risks with additional information pertinent to the risks of adverse effects from the use of the at least one drug of interest; permitting at least one remote user to access such data through the World Wide Web upon proper authentication; permitting the at least one remote user to identify the at least one drug of interest; permitting the at least one remote user to select data stored in the one or more servers relevant to the safety of using the at least one drug of interest; permitting the at least one remote user to analyze safety issues resulting from use of the at least one drug of interest, and permitting the at least one remote user to display such data and analysis.

The web based system described provides patients, government health agencies and physicians with details of drug-drug interactions, adverse effects, including non-responsiveness, and resistance. The system relates to some extent, to clinical, genetic and metabolic inputs. It provides alternative treatments.

It will be appreciated that the physician has limited time with patients and has to access relevant information as quickly and efficiently as possible. Improvements in drug prescription affect the quality of life for the patient and benefit society as a whole.

Despite the great steps forward with computer access to information, the physician's time is at a premium. There is an ongoing need for more effective treatments, cost savings to the health system and faster prescription of more appropriate drug regimes, whilst minimizing the risk of adverse interactions.

Embodiments of the present invention address these needs.

SUMMARY OF THE INVENTION

The present invention is directed to providing a platform accessible by a user from a web browser and/or an electronic medical record (EMR) for providing the user with information regarding a patient's drug regimen as well as generating alerts concerning potential adverse effects to the patient from taking a cluster including a plurality of pharmaceutical preparations; the platform being in data communication with, and configured to obtain information from, at least one database and at least one tool for processing the cluster of pharmaceutical preparations in accordance with the information to generate the alerts to the user.

Typically, the potential adverse effects include side effects of drug-drug interactions and effects of the patient's genetic profile on drug efficacy.

In an example embodiment, the at least one database includes an electronic medical record system including a database of patient records.

In an example embodiment, the at least one database includes details of estimated deviations in drug serum levels in response to concomitant administration of other drugs as well as the genetic profile of the patient.

In an example embodiment, the at least one database includes clinical data concerning at least the cluster of pharmaceutical preparations.

In an example embodiment, the at least one tool for processing the cluster of pharmaceutical preparations includes a Shared Adverse Side Effect Predictor for analyzing the plurality of pharmaceutical preparations in the cluster for side effects common to at least two of the pharmaceutical preparations.

In an example embodiment, the Shared Adverse Side Effect Predictor displays the side effects common to at least two of the pharmaceutical preparations in a user interface displayable on a web browser or EMR.

Additionally or alternatively, the Shared Adverse Side Effect Predictor displays an alert in a user interface displayable on the web browser or EMR.

In an example embodiment, the at least one tool for processing the cluster of pharmaceutical preparations includes a Health Care Burden Estimator for predicting costs resulting from the potential adverse effects to the patient from taking the cluster including a plurality of pharmaceutical preparations.

In an example embodiment, the predicted costs include at least one of the group consisting of admission to hospital, duration of hospitalization, referrals to emergency rooms, sessions with general-practitioners and sessions with specialist physicians.

In an example embodiment, the predicted costs include a cost associated with at least one diagnostic technique of the group including computed tomography, Magnetic Resonance Imaging, Ultra Sound and X-ray.

In an example embodiment, the platform includes an Alternative Drug Suggestion Mechanism for suggesting at least one alternative drug to replace at least one pharmaceutical preparation in a plurality of pharmaceutical preparations.

In an example embodiment, the Alternative Drug Suggestion Mechanism assesses potential adverse affects of alternatives and suggests alternatives that do not generate more than a preconfigured significance threshold number of alerts regarding potential adverse affects.

In an example embodiment, the Alternative Drug Suggestion Mechanism is configured to systematically suggest alternatives to each pharmaceutical preparation in a plurality of pharmaceutical preparations until no more than an acceptable number of alerts regarding potential adverse effects above a preconfigured significance threshold are generated.

In an example embodiment, the platform includes a Rules-&-Alerts Engine including rules for generating alerts of potentially harmful effects of drug combinations.

Typically, the Rules-&-Alerts Engine includes at least one rule selected from pre-defined rules and rules defined by the user.

In an example embodiment, the Rules-&-Alerts Engine includes at least one rule relating to a healthcare burden of the cluster of pharmaceutical preparations.

In an example embodiment, the user interface is accessible via a stand-alone web platform and/or via an icon displayed in the electronic medical record (EMR) of the patient.

In an example embodiment, a warning is displayed in the electronic medical record (EMR) of the patient if the platform generates an alert for the cluster of pharmaceutical preparations prescribed.

A second aspect of the invention is directed to a method of improving poly-pharmaceutical prescription to a patient by displaying alerts to a user responsive to potential adverse effects of suggested combinations of drugs, where at least one alert relates to a predicted healthcare burden of the drugs taken in combination, such that the healthcare burden relates to healthcare expenditures including at least one of admission to hospital, duration of hospitalization, referrals to an emergency room, visits to a general practitioner, appointments with specialist physicians and costs associated with diagnostic techniques selected from the group including computed tomography, Magnetic Resonance Imaging, Ultra Sound and X-ray imaging.

Thus, a system and method are provided for optimizing a drug regimen of a patient, where the system is configured to access at least one database containing drug information, and where, when a user suggests that the patient receives a regimen of drugs, and three or more of the drugs are found in the database, the system analyzes the combined effect of each 2-way combination on the metabolism and adverse effect profile of each of the other drugs in the regimen.

In an example embodiment, a system for optimizing a drug regimen of a patient is provided, where the system is configured to access a database containing drug information, and where, when a user suggests that the patient receive a regimen of drugs, and 2 or more of the drugs are found in the database, the system analyzes the interaction of the patient's genotype with each 2-way drug combination of the drugs in the database within the regimen.

In an example embodiment, a system for optimizing a drug regimen of a patient is provided where the system is configured to access a database containing drug information, and where, when a user suggests that the patient receive a regimen of drugs, and information regarding at least two of the drugs are found in the database, the system analyzes the health-care burden of each 2-way combination in said regimen.

In an example embodiment, the system analyzes the healthcare burden for three or more drugs.

In an example embodiment, the system analyzes the healthcare burden for the entire regime.

In an example embodiment, there is provided a system for optimizing a drug regimen of a patient receiving at least one drug, where the system is configured to access a database containing drug information, and where, when a user suggests that the patient receive a regimen of drugs, and information concerning a plurality of the drugs are found in the database, the system generates an alert when a significant deviation of the effective concentration of at least one of said drugs, or an adverse effect, is expected, where the parameters of the alert are set by the user.

Yet another aspect of the invention is directed to a system for optimizing a drug regimen of a patient receiving at least one drug, where said system is configured to access a database containing drug information, and where the system is adaptable to the preferences of individual users.

BRIEF DESCRIPTION OF TE FIGURES

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of preferred embodiments of the present invention only, and are presented in the cause of providing what is believed to be the most useful and readily understood description of the principles and aspects of the invention. In this regard, no attempt is made to show structural details of the invention in more detail than is necessary for a fundamental understanding of the invention; the description taken with the drawings making apparent to those skilled in the art how the several forms of the invention may be embodied in practice.

FIG. 2 is an exemplary screen of the GENELEX™ system provided for information purposes.

FIG. 3 is an exemplary screen of the FIRST DATA-BANK™ system provided for information purposes.

FIG. 12 shows how a Healthcare Estimator uses rules and alerts that are generated from data extracted from different databases and processed by the DDI+ Platform and applied to drug clusters for each patient, according to an example embodiment of the present invention.

FIG. 14 shows a table of alerts, which may be output according to an example embodiment of the present invention.

DETAILED DESCRIPTION

Patients treated with a number of drugs often exhibit substantial deviation from expected/desired serum levels, significant adverse side effects, lack of efficacy, as well as much increased health expenditures due to complex drug-drug and gene-drug interactions. It is estimated that between 5% and 30% of those who each receives 2-5 drugs exhibit severe clinical consequences such as side effects, non-responsiveness and toxicity.

Embodiments of the present invention address this issue by presenting the user, typically the physician, with relevant clinical and pharmacokinetic/pharmacodynamic data regarding patients and other members of the insured population, for quick comprehension with all relevant information summarized for viewing in a single glance, via a user-friendly GUI.

It will be appreciated that physicians typically see patients for very short consultations and are required to diagnose and to offer treatment, generally by prescription, in a small time period. This is typically the case whether the doctor is a general practitioner meeting a patient for an appointment in the clinic, or is a specialist making rounds in hospital wards. It is advantageous for the physician to be able to access the patient's health records, to be notified of alerts according to user pre-definitions without having to look for the information, to be able to simulate the likely effect of different drugs or alternative dosage regimens and to be efficiently alerted regarding shared side effects in minimal time.

Aspects of present invention are directed to providing a platform, designed either as a stand-alone web platform or as part of the patients' electronic medical records (EMRs) by integration with the EMR. This platform is referred to herein below as the DDI+™ Platform.

In the various embodiments, the user is provided with access to the DDI+ via the EMR of the patient or via a stand-alone web system.

The DDI+ platform presents to the physician the list of currently prescribed drugs extracted from the patient's electronic medical records (EMR) together with up-to-date research extracted from the medical literature and/or simulated by simulations based on various algorithms and models. The DDI+ platform predicts likely effects of alternative drug treatments, including generic equivalents, alternative treatments and different dosage regimens. In example embodiments, the assessments are based on rules and algorithms that are run in the background and displayed response to a physician's/use's request in a clear and concise manner, without noticeable time lags (e.g., within few seconds).

The deviation from serum levels of drug-drug interactions, drug-gene interactions and metabolic pathways is estimated.

Figure 1:
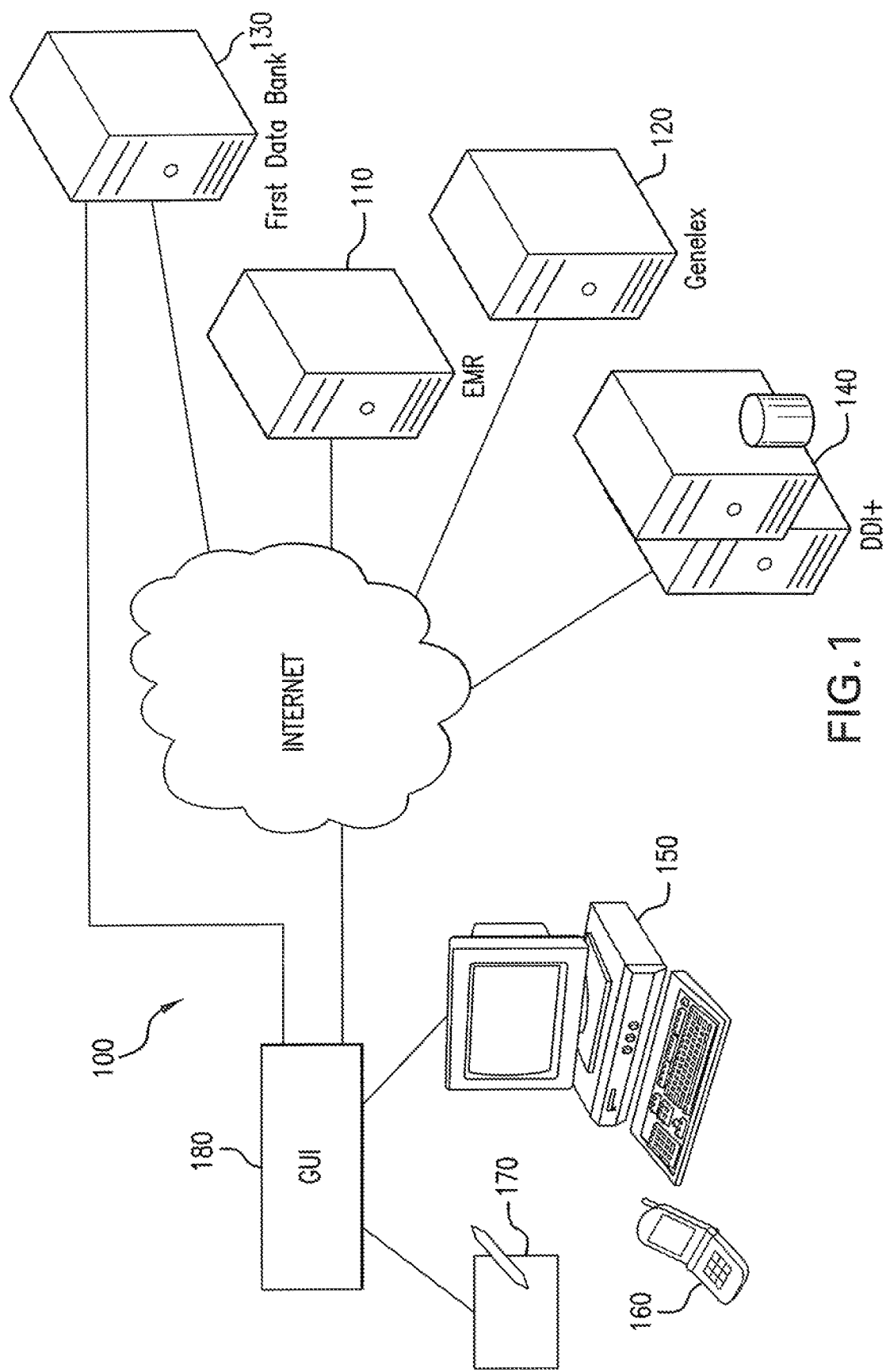
FIG. 1 is a schematic illustration of a system of the invention supported by the Internet, according to an example embodiment of the present invention.

FIG. 1 shows a system according to an example embodiment of the present invention. The system 100 is a web based system for improving the pharmaceutical treatment for a patient. The system 100 may include an EMR system 110 of a health care provider such as an HMO, containing an Electromagnetic Medical Record EMR for the patient, including patient history and current drug regime, and at least one database for providing supplementary information for improving prescriptions.

By way of non-limiting example, the databases provided may include the commercially available GENELEX™ database 120 for assessing the likely physiological effect of the drug on serum levels due to interactions, and the commercially available FIRST-DATABANK™ database (FDB) 130 that mainly reports on clinical drug-drug interactions, mostly extracted from the medical literature. The system also includes a proprietary DDI+ Platform 140 for extracting information from the various databases and for analyzing and processing the collected data, generating alerts at pre-configured conditions, calculating the estimated HealthCare burden and shared side effect and for suggesting safe alternative poly-pharmacology regimens.

In an example embodiment, the DDI+ Platform 140 operates in the background and generates alerts in accordance with user-definable rules. The system is accessible over the Internet from physicians' web browsers which may be running at a personal computer 150, a mobile phone 160 and/or a tablet 170, and the gathered and processed data may be displayed in a comprehensive, intuitive and easily navigable graphical user interface (GUI) 180 on the screen of the computer 150, mobile phone 160 or tablet 170 of the physician.

For specific drug combinations, the estimated deviation of drugs from their expected serum levels is calculated by the GENELEX™ database 120, and interactions are predicted by the FIRST-DATABANK™ database 130. Data from a number of databases such as these is combined and presented via a single, intuitive GUI 180. In example embodiments, the patient's genetic profile is used as one of the inputs together with metabolic aspects affecting poly-pharmacy and potential deviations from expected serum levels.

Warnings and alerts are displayed in accordance with physician settings. For example, shared side effects of multiple drugs within the same drug cluster will result in an alert showing, since shared side effects are particularly harmful.

GENELEX™ Database 120

Figure 2:
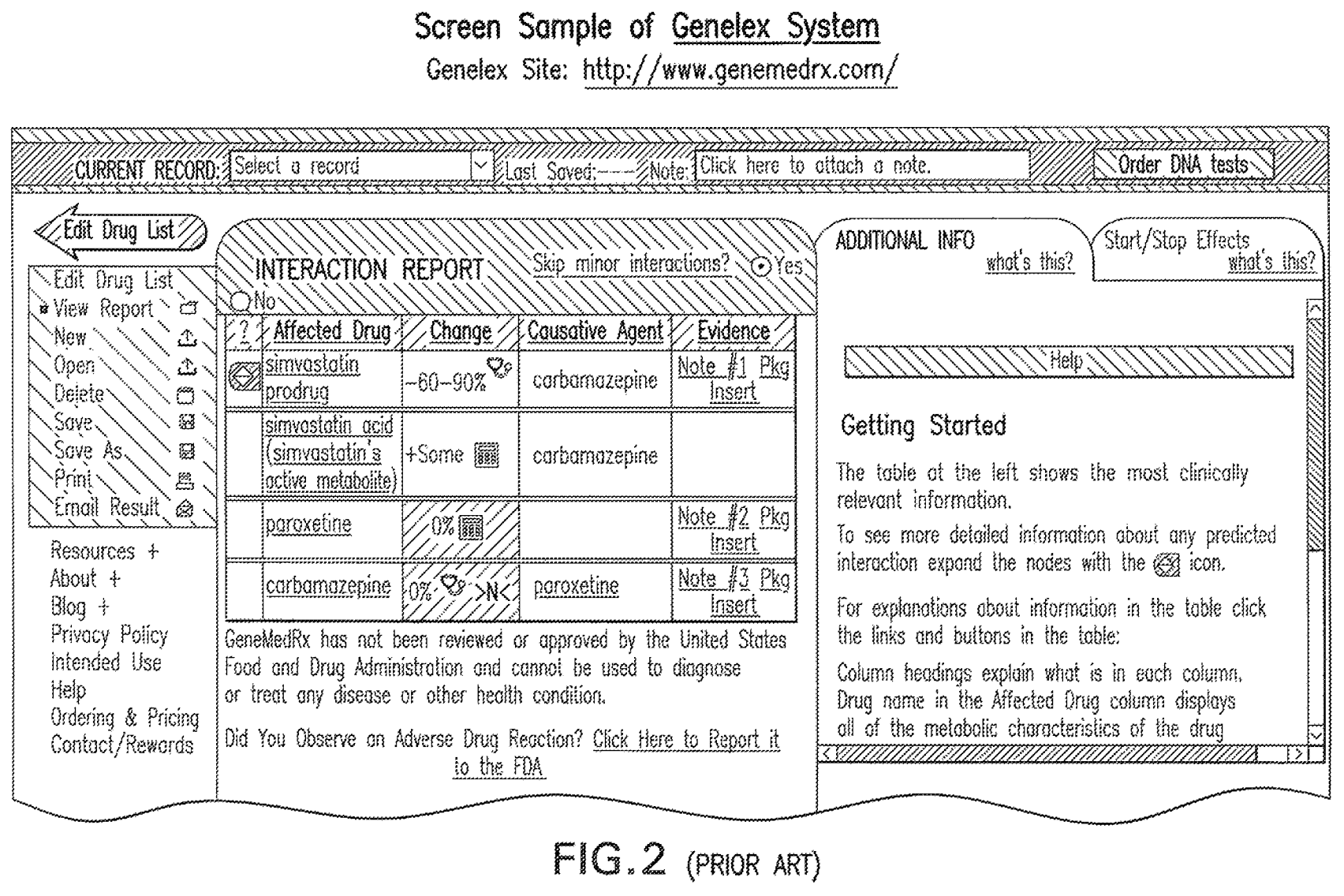

The effects of drug combinations on blood serum levels are predicted by commercially available software such as the GENELEX™ database and program. By way of illustration, FIG. 2 shows a sample screen display of the GENELEX™ system.

The following information, describing capabilities of the GENELEX™ system, is taken from the GENELEX™ website.

Virtually every pathway of drug metabolism, transport and action is susceptible to genetic variation. It is estimated that 20%-95% of individual variability is genetic based. Within the top 200 selling prescription drugs, 59% of the 27 most frequently cited in ADR studies are metabolized by at least one enzyme known to have gene variants that code for reduced or non-functional proteins. This compares with 7% of a random selection from the top 200 list. Many other factors such as age, physiological functioning and concomitant disease am known and can be accounted for, leaving the genotype of the patient as a major unknown factor in the prescribing of medicines.

GENELEX™'s DNA Drug Reaction tests for the highly polymorphic cytochromes, CYP2D6, CYP2C9, and CYP2C19. These enzymes process half of the most commonly prescribed drugs, including many with narrow therapeutic indices and frequent participation in drug-drug interactions. An estimated 50% of patients have genetic variations in these genes that lead to altered or absent function resulting in elevated patient susceptibility to adverse drug reactions. Genotyping to avoid ADRs is a dependable tool to improve treatment.

It has been estimated that anywhere from one in five (1/5) to two out of three (2/3) members of the general population exhibit genetic abnormalities regarding the rate at which drugs are metabolized from their systems. In example embodiments, a saliva/bloodsample from the patient is tested to determine the genotype and phenotype of the patient, and the metabolic activity of the various enzymes, such as the hepatic CYP450 enzyme, that affects the rate of elimination of drugs from the patient's serum. This information is made available to the physician and is used to suggest corrections to dosages.

CYP2D6 (cytochrome P450 216) is the best studied of the drug metabolizing enzymes (DMEs) and acts on one-fourth of all prescription drugs, including the antidepressant and anxiolytic class of drugs named selective serotonin reuptake inhibitors (SSRIs) and tricylic antidepressants (TCAs), beta-blockers such as Inderal and the Type 1A antiarrhythmics. Approximately 10% of the population has a slow acting form of this enzyme and about 7% has a super-fast acting form. Thirty-five percent of patients are carriers of a non-functional 2D6 allele, especially elevating the risk of ADRs when these individuals are taking multiple drugs. Drugs that CYP2D6 metabolizes include Prozac, Zoloft, Paxil, Effexor, hydrocodone, amitriptyline, Claritin, cyclobenzaprine, Haldol, metoprolol, Rythmol, Tagamet, tamoxifen, and the over-the-counter diphenylhydramine drugs, Allegra, Dytuss, and Tusstat. CYP2D6 is responsible for activating the pro-drug codeine into its active form and the drug is therefore inactive in CYP2D6 slow metabolizers.

CYP2C9 (cytochrome P450 2C9) is the primary route of metabolism for Coumadin (warfarin) and Dilantin (phenytoin). Approximately 10% of the population are carriers of at least one allele for the slow-metabolizing form of CYP2C9 and may be treatable with 50% of the dose at which normal metabolizers are treated. Other drugs metabolized by CYP2C9 include Amaryl, isoniazid, sulfa, ibuprofen, amitriptyline, Hyzaar, THC (tetrahydrocannabinol), naproxen, and Viagra.

CYP2C19 (cytochrome P450 2C19) is associated with the metabolism of carisoprodol, diazepam, Dilantin, and Prevacid.

CYP1A2 (cytochrome P450 1A2) is associated with the metabolism of amitriptyline, olanzapine, haloperidol, duloxetine, propranolol, theophylline, caffeine, diazepan, chlordiazepoxide, estrogens, tamoxifen, and cyclobenzaprine.

NAT2 (N-acetyltransferase 2) is a second-step DME that acts on isoniazid, procainamide, and Azulfdine. The frequency of the NAT2 "slow acetylator" in various worldwide populations ranges from 10% to more than 90%.

Warfarin (Coumadin) Target Dose Safety Test (2C9 and VKORC1) predicts the maintenance dose of warfarin to within 1.5 mg per day, or less.

The physician can assess the effect of varying drug dosages and of substituting one drug for another to the patient's health and wellbeing, to minimize the occurrence of alerts and to reduce cost of treatment without compromising the patient's interests.

FIRST DATABANK™ (FDB) 130

The FIRST DATABANK™ database (FDB) 130 is a commercially available collection of databases that provides indications of drug-drug interactions based on medical literature. FIRST DATABANK™ has developed comprehensive reference products in electronic form, for quick and direct access to detailed drug clinical and pricing information. By way of illustration, FIG. 3 shows an example screen of the FIRST DATABANK™ database 130 interface.

The following information is taken from the FIRST DATABANK™ website and is provided for information purposes.

The drug knowledge bases include DIF API and NDDF Plus, which is one of the industry's most widely-used and highly regarded sources of drug information. Along with descriptive drug information, unique identifiers and pricing data, NDDF Plus offers an extensive array of clinical decision-support modules. FIRST DATABANK™ also provides powerful content integration software that enables developers to easily embed drug information into various applications, quickly and economically.

The DDI+ Platform 140

Figure 4:
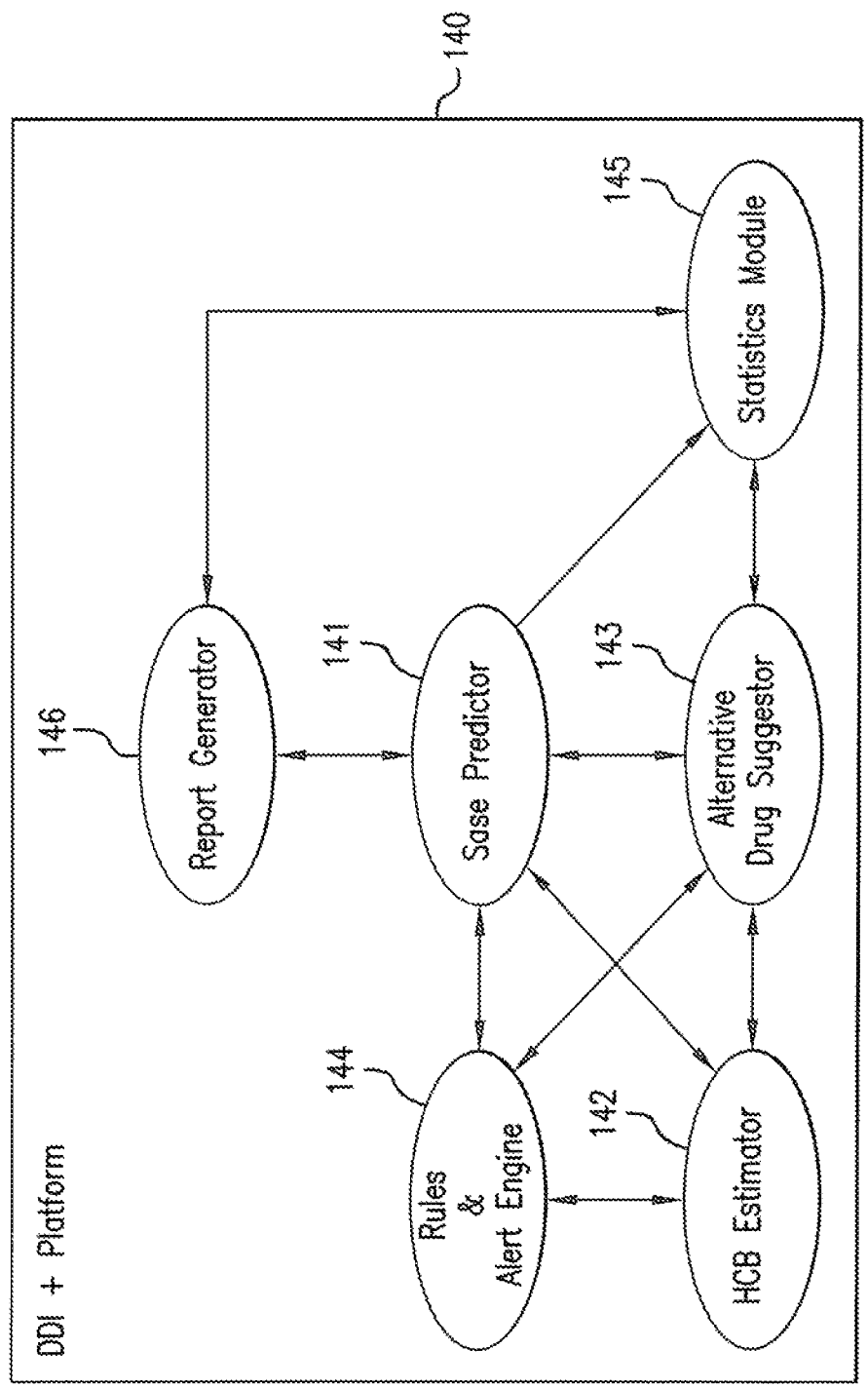
FIG. 4 is a functional block diagram of the DDI+ 140, according to an example embodiment of the present invention.

FIG. 4 is a functional block diagram of the DDI+ Platform 140 in accordance with an example embodiment of the present invention. The DDI+ Platform 140 may include a:

1. A Shared Adverse Side Effect Predictor (SASE Predictor) 141
2. A HealthCare Burden Estimator (HCB Estimator) 142
3. An Alternative Drug Suggestion Mechanism (ADS Mechanism) 143
4. A Rule-&-Alerts Engine (R&A Engine) 144 having pre-defined and user configurable rules that generate alerts
5. A Statistics module 145
6. A Reporter 146
7. A Graphical User Interface (GUI) 180

Example embodiments of the DDI+ Platform 140 are integrated with the electronic medical record EMR of the health maintenance organization (HMO) and work in the background, providing notifications only upon significant variation from user configurable conditions thereby not interfering with doctors' work routine. In some embodiments the default display of the electronic medical record EMR is the traditional display, with the DDI+ accessible via an icon, so that physicians can continue working without interference and be notified upon violation of critical pre-defined and user configurable conditions by alerts generated by the Rules & Alerts engine 144 of the DDI+ Platform 140.

Example embodiments also track and flag homeopathic treatments and food supplements without prescription drugs.

There are, however, some types of alerts that can be ignored in a specific scenario and DDI+ is a learning platform that can be configured to allow the user to ignore some specific alerts. For example, an alert regarding adverse effects on fertility will be of no interest per so when prescribing drugs for a male patient who has undergone a vasectomy or for a post-menopausal female patient. Likewise, a risk of blurred vision from a drug-drug interaction is not of concern to a blind patient.

It will also be appreciated that although various drug combinations may be contra-indicated based on their monographs/regulatory requirements etc., nevertheless, in certain instances and based on the physicians' clinical judgment, administering such combinations may be possible or even recommended. Such instances might be for patients who have serious medical conditions and respond only to such specific combinations or in cases where patients need to receive off-label drugs because, for example, other treatments have proven ineffective. Sometimes, there are drug shortages and preferred drugs am not available.

Thus, in an example embodiment of the present invention, DDI+ Platform 140 is a learning platform that enables the physician to ignore specific Alerts. This feature enables the platform to be conformed to the physician's clinical judgment and specific needs. In such implementations, the system "learns" the ignored alerts and excludes them from the original pre-defined rules, so alerts for specific combinations of physician, patient, rules and causative drugs will not be displayed. If required, the physician can reactivate ignored rules and cause previously not displayed alerts to be displayed by configuring the display settings of the DDI+ Platform 140 and the GUI 180.

Via the Statistics Module 145 and Reporter 146, the DDI+ Platform 140 logs the override-alerts for further auditing and generates reports to both the physician and management.

The GUI 180

Figure 5:
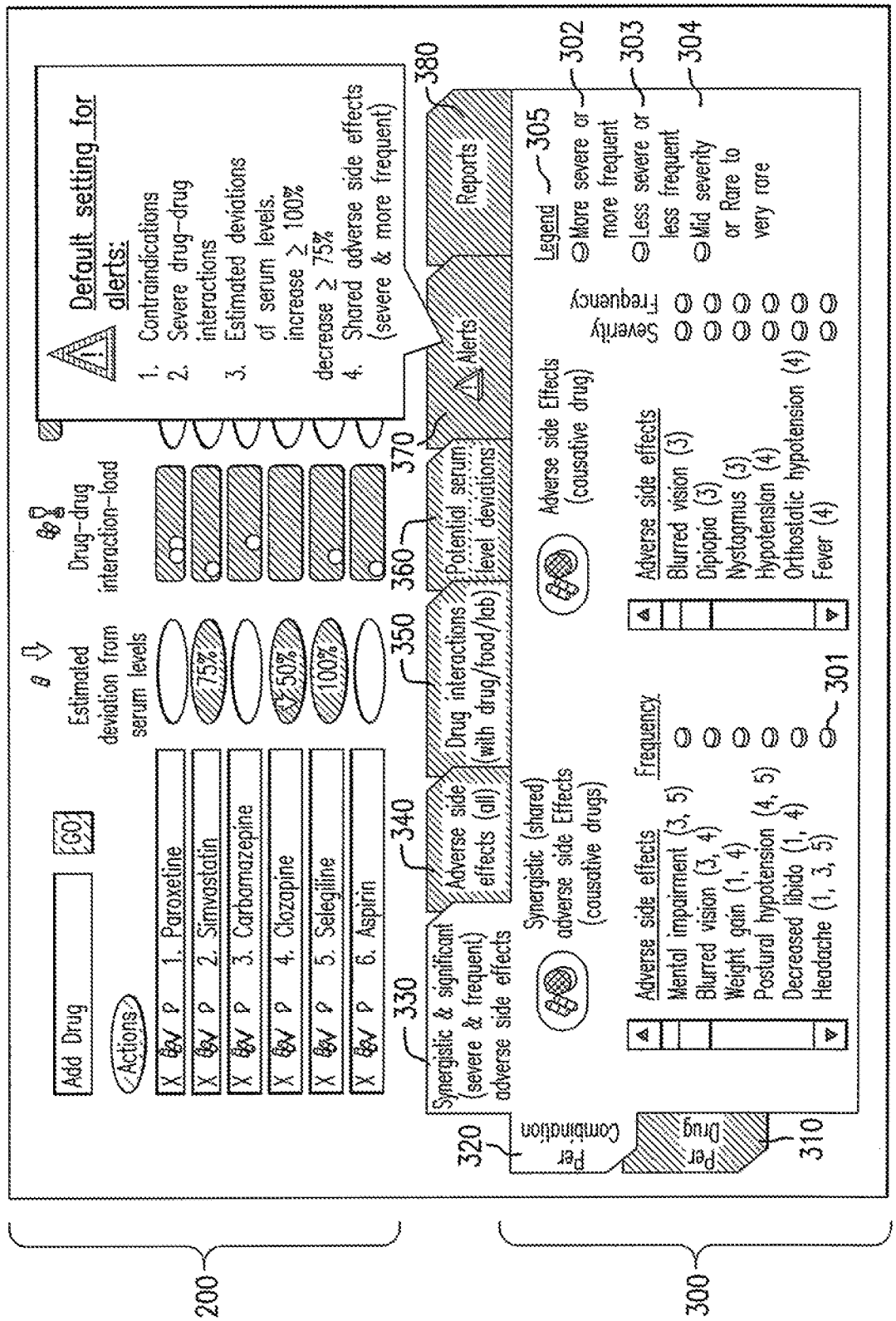
FIG. 5 is a screen capture of the main screen of an exemplary embodiment of the GUI, showing the drugs prescribed the estimated deviation from serum level data extracted from the Genelex database, the drug-drug interaction data from the First-Databank (FDB), and the proprietary alerts of the DDI+ in an upper section, and tabbed windows for more detail in a lower section.
Figure 6:
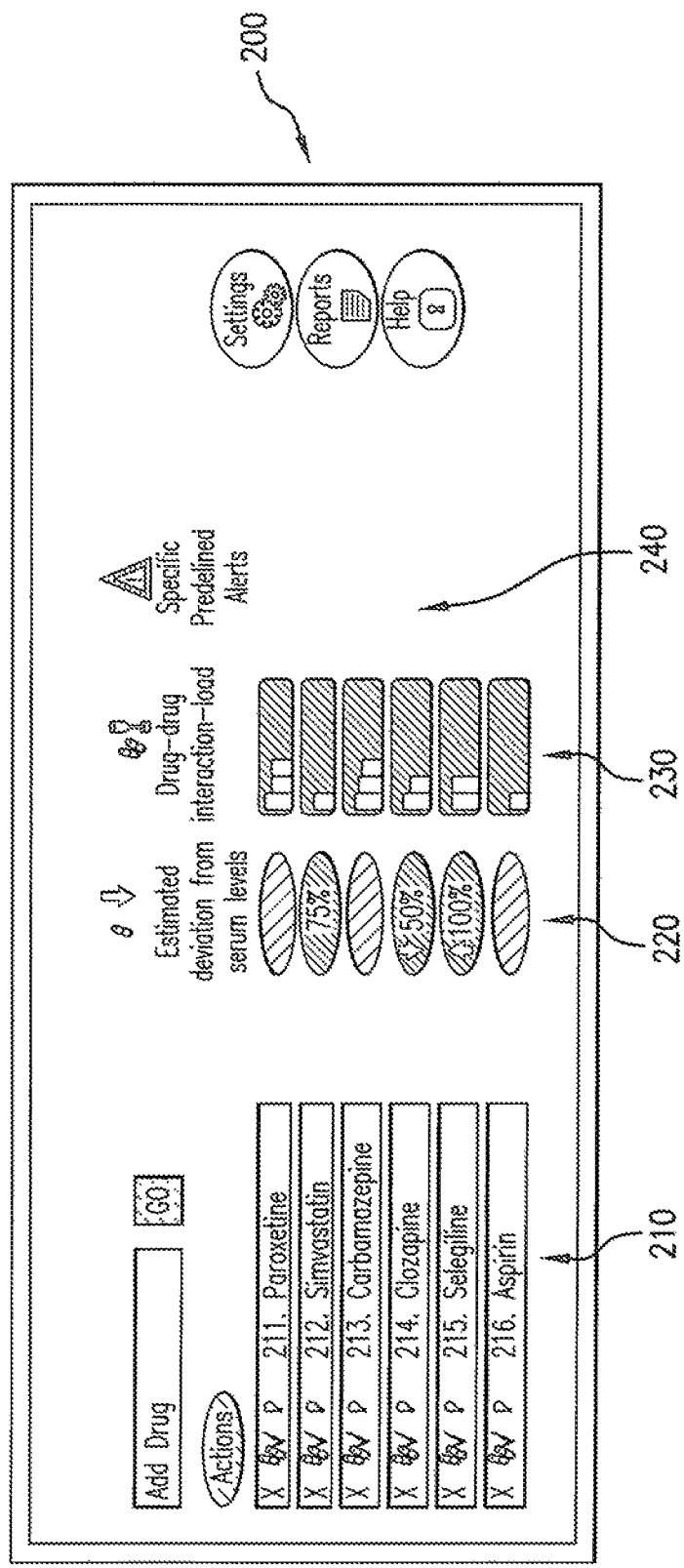
FIG. 6 is a screen capture of an upper section of a main screen of a GUI providing a comprehensive view of results and alerts generated by a system at a single glance, according to an example embodiment of the present invention.

With reference to FIG. 5, an example main screen 190 of the GUI 180 of the DDI+ Platform 140 is shown. The main screen 190 includes an upper part 200 and a lower part 300. The upper part 200 provides an immediate view of the currently considered list of drugs, results of interactions and serum level deviations created by the various tools and databases available, and alerts generated by the DDI+ Platform 140. The lower part 300 provides an interactive intuitive drill down display for viewing further information regarding adverse predicted effects and the like. In FIG. 6, the upper part 200 of the main screen 190 is shown in more detail.

Thus with reference to FIG. 6, the upper part 200 of the main screen 190 of the GUI 180 of the system 100 is shown for a patient. In the left column 210, the drugs prescribed are automatically shown using the trade names used Paroxetine 211, Simvastatin 212, Carbamazepine 213, Clozapine 214, selegiline 215, and Aspirin 216. In the second column 220, estimated positive and negative deviations from serum level is given as a percentage of efficacy, based on input from the GENELEX™ database 120. In the third column 230, drug-drug interaction data based on information provided by the FIRST DATABANK™ (FDB) database 130 is shown in a graphical manner, where, for example, the height, number, and/or color of bars indicate the severity of the interaction.

In the fourth column 240, specific predefined alerts are displayed in accordance with rules in the DDI+ Platform 140. The alerts may also refer to the data regarding potential deviation of serum levels and drug-drug interaction (second and third columns), and, in example embodiments, may be highlighted in red in the upper part to draw immediate attention to the alerts. The rules may be created by the HMO or by the physician and are responsive to the physician's prescribing, including the possibility to consider a patient's specific profile, such as gender, age, pregnancy, smoking, and the like.

Where the DDI+ platform 140 is integrated with the EMR, the default list of drugs shown is the list of drugs actually prescribed, as extracted from the EMR.

The user is able to add or subtract drugs to the list in the left column 210 of the upper part 200 of the main screen 190 and simulate the probable effect on the patient, by viewing the changes in the second column 220 showing how the drug affects the estimated deviation from serum level given as a percentage of efficacy, based on input from the GENELEX™ database 120, and the drug-drug interaction data based on information provided by the FIRST DATABANK™ (FDB) database 130 in the third column 230. If the addition of the drug contradicts one of the rules configured into the DDI+ Platform 140, alerts are generated and displayed in the fourth column 240.

In an example embodiment of the present invention, the alerts may relate to the health care burden as calculated by the Health Care Burden Module 142 discussed hereinbelow in more detail.

By virtue of the ease of use, clear presentation in the upper part 200 of the main screen 190 and the described user-configurable rules and alerts, the physician is able to quickly and efficiently optimize prescriptions.

Referring back to FIG. 5, the interface is designed to provide the physician or other user with information of interest in a clear and uncrowded manner. The interface of FIG. 5 includes side tabs to selectively view further data per specific drug 310 or per combination 320, and can then view the predicted effects of combinations by selecting an appropriate tab such as Shared Side Effects 330, adverse side effects 340, Drug Interactions 350 such as drug-drug, drug-food and drug-gene, potential serum level deviations 360, alerts 370 and reports 380.

In an example embodiment, the user is able to select tabs, with the tab selection affecting the information displayed. Thus, choosing the appropriate tab and specific drugs from the list of drugs in the first column 210, causes more associated information to be displayed in the lower part 300 of the main screen 190, configured in the embodiment shown as a card index (tabs), for intuitive navigation. It will be noted that the lower part uses intuitive and graphical indications 301 such as red 302, yellow 303 and green 304 lights, and in some embodiments a legend 305 is displayed so that the meaning, though intuitive, is clearly displayed as well.

The patient's electronic medical records and information regarding the drugs of interest are displayed to the physician in an intuitive manner. The physician has freedom to prescribe as the physician sees fit, but due to the availability of significant decision-support information and the intuitive way it is displayed via the GUI 190 and using alerts, despite the small amount of time that the physician typically can dedicate to the patient, more appropriate treatment is facilitated.

As configured in the main described and illustrated embodiment, in the GENELEX™ database 120, patient factors are set in a manner similar to drugs. In the FIRST DATABANK™ database 130, patient factors are considered as medical conditions and given as the cause. In the DDI+ 140, although the patient factor is treated, in some aspects, as another drug on the list, the main screen 190 of the GUI 180 shows the patient factors in a separate list, presented differently from the drug list in the first column 210. It will, however, be appreciated that other display configurations may be employed.

Figure 7:
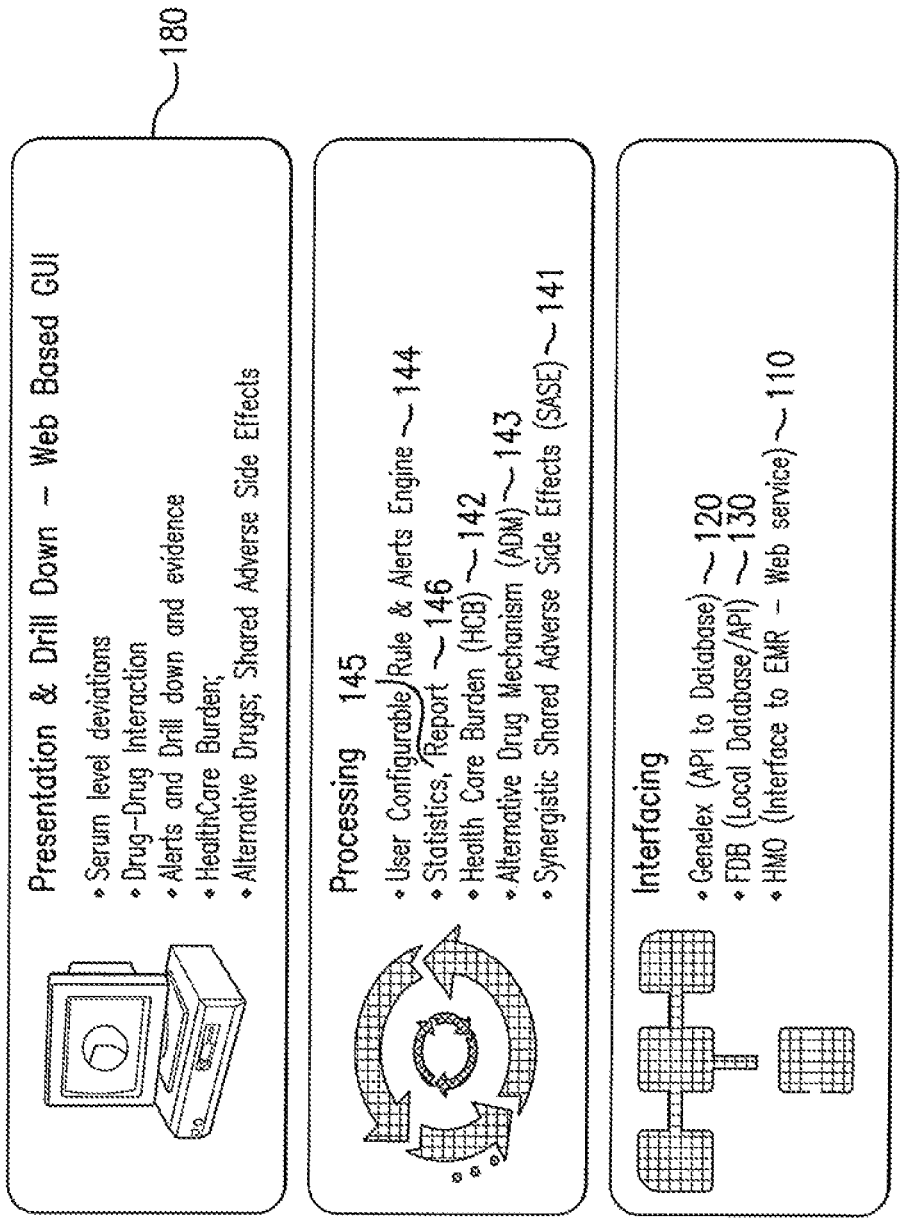
FIG. 7 is a hierarchical model of the DDI+ showing logical layers thereof, according to an example embodiment of the present invention.

With reference to FIG. 7, a logical layer model of the DDI+ Platform 140 is shown, according to an example embodiment of the present invention. The DDI+ Platform 14 interfaces with the EMR system 110 of the HMO to obtain patient specific information, with the GENELEX™ database 120 to obtain effects on serum levels due to patient physiology and genetic profile and drug interactions, and with the FIRST DATABANK™ database 130 to obtain drug-drug interaction data from the literature. The DDI+ Platform 140 processes available data using the Shared Adverse Side Effects predictor (SASE predictor) 141, the Healthcare Burden Estimator 142, the Alternative Drug Suggestor (ADS) 143 and the user configurable Rules & Alerts Engine 144. Statistics and reports are made available by the Statistics Module 145 and the Report Generator 146. Serum level deviations, drug-drug interactions, health care burden, alternative drugs, shared adverse side effects and alerts are displayed in the web based GUI 180, and the user is able to intuitively drill down and access evidence, relevant scientific data, etc.

The various components and features of the DDI+ Platform 140 are now presented in more detail.

The Health Care Burden—a New Approach to Simultaneously Improve Poly-Pharmaceutical Treatments and Reduce Healthcare Expenditure A retrospective data analysis was conducted on a sample of 111 randomly selected adult ambulatory patients with multiple chronic conditions that were being treated by at least 5 drugs and typically eight or more.

The patients were selected due to their undergoing treatment under the care of a large number of different physicians, thereby ruling out the prescriptive effects of specific physicians.

The analysis looked at patients' medical records to see the specific drugs that had been prescribed over time.

Known interactions between drugs were flagged and where efficacy was expected to be adversely affected by combinations, this was also flagged. The combined information available from GENELEX™ Database and from FIRST DATABANK™ database was used to generate alerts and significant side effects common to two or more of the drugs were flagged.

The list of patients was ordered by the total number of flags generated for each drug cluster per patient, where a cluster refers to a combination of two or more drugs.

This simulation resulted in two groups of patients. One group of 77 patients had significantly more flagged interactions than the remaining 34.

The group of 77 patients had an average age of 69.6 and 36.4% of them had Ischaemic Heart Disease IHD, 90% suffered from hypertension, 72.7% had diabetes and 62.35% had hyperlipidemia. The remaining 34 patients had an average age of 72.8 and 32.3% of them had Ischaemic Heart Disease IHD, 91.1% suffered from hypertension, 70.6% had diabetes and 64.7% had hyperlipidemia. Rigorous statistical analysis indicated that as far as age and these chronic conditions were concerned, there was no significant difference between the two populations.

However, the first group of 77 patients was characterized by significantly higher incidence of visits to the emergency room ER, admission to hospital, days in hospital and expensive and time consuming imaging techniques.

Figure 8:
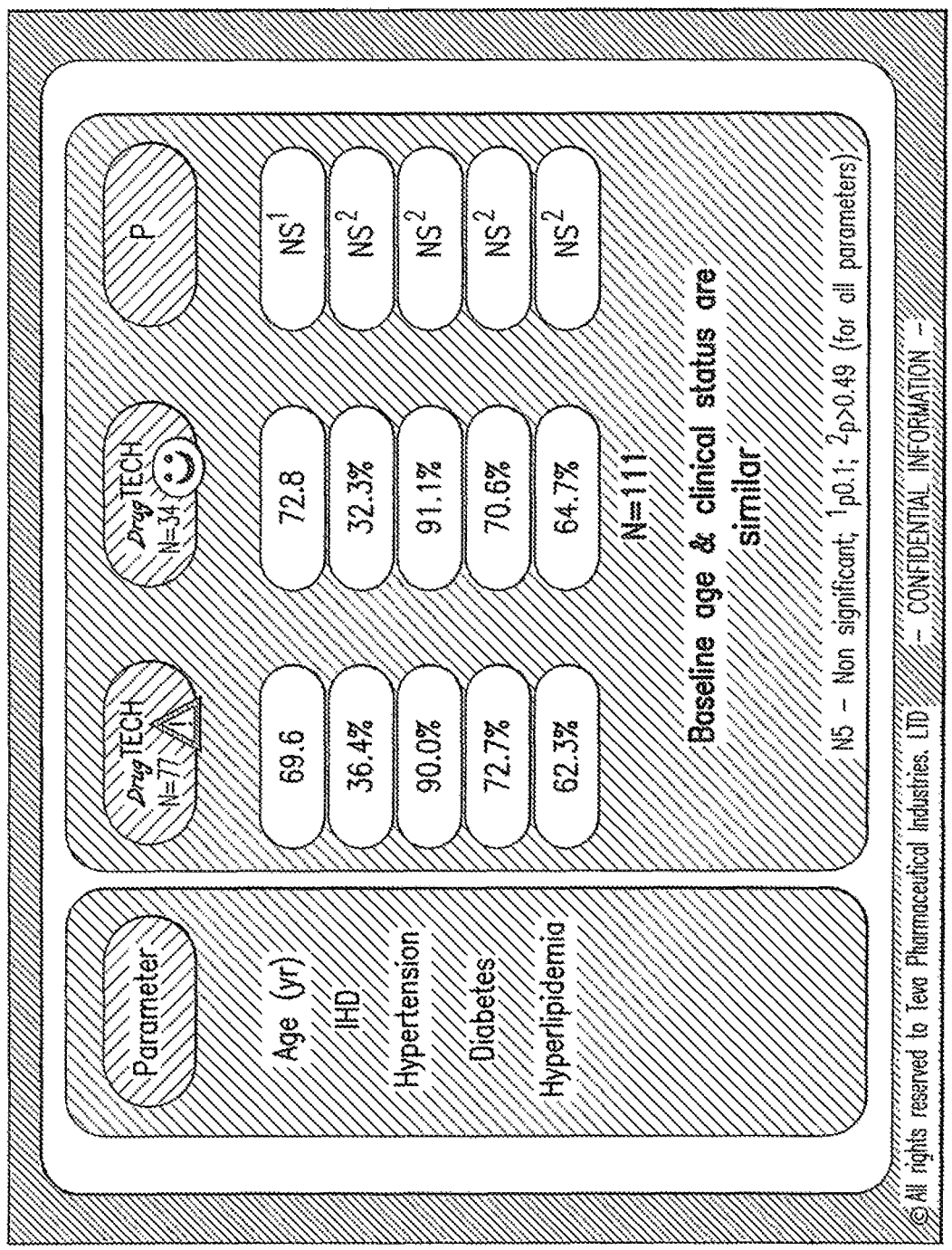
FIG. 8 is a summary table of results of a retrospective study conducted on patients of a specific HMO showing an effect of alerts on first and second populations in terms of illnesses, according to an example embodiment of the present invention.

FIG. 8 summarizes the age and clinical status details for the two groups.

Figure 9:
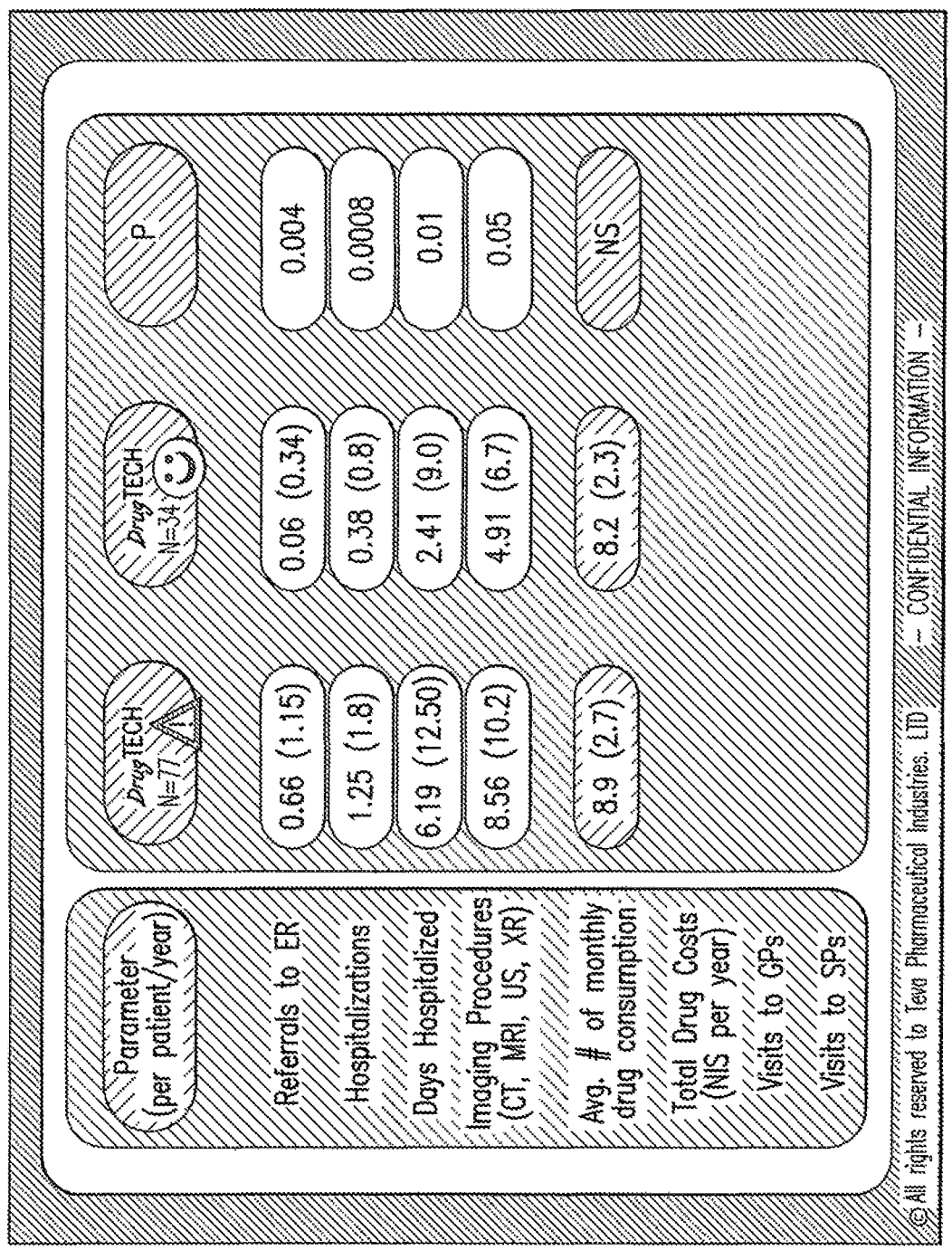
FIG. 9 is a summary table of results of a retrospective study conducted on patients of a specific HMO showing an effect of alerts on first and second populations in terms of cost factors contributing to the health care burden, according to an example embodiment of the present invention.

FIG. 9 summarizes the contributory factors to the total health care burden. It will be noted that the cost of drugs was actually higher, though not significantly, for the first group. The other costs examined were significantly higher for the first group. These costs are also more significant than the difference in the costs of alternative drugs, which, due to the intense competition between manufacturers, is not surprisingly, not a significant part of the overall cost.

This analysis clearly demonstrates the strong correlation between the number of flagged events and their severities and the associated HealthCare costs related to quality of the treatment.

By converting such flagged adverse effects into alerts and using the information pro-actively, the inventors have discovered that an alert system can be configured to alert the physician of adverse interactions between drugs, serum levels and side effects, and can be used to improve poly-pharmaceutical treatment.

The total healthcare burden, including not merely the cost of the drugs themselves, but also expensive diagnostics, hospital visits, days of hospitalization, appointments with the general practitioner, appointments with specialists, visits to the Emergency Room may be a good indicator of the success of a specific drug regimen. This is being tested in a large scale research program that is being conducted on the physicians and patients of an HMO.

The total health care burden is an accurate indication of the well-being of the patient considered holistically and not merely as the sum of the symptoms, since overall treatment costs are generally inversely correlated with a patient's well-being. It will be appreciated that minimizing the healthcare burden of a patient by improving drug prescription can also save the IMO vast sums of money.

The Shared Adverse Side Effects Predictor 141

Figure 10:
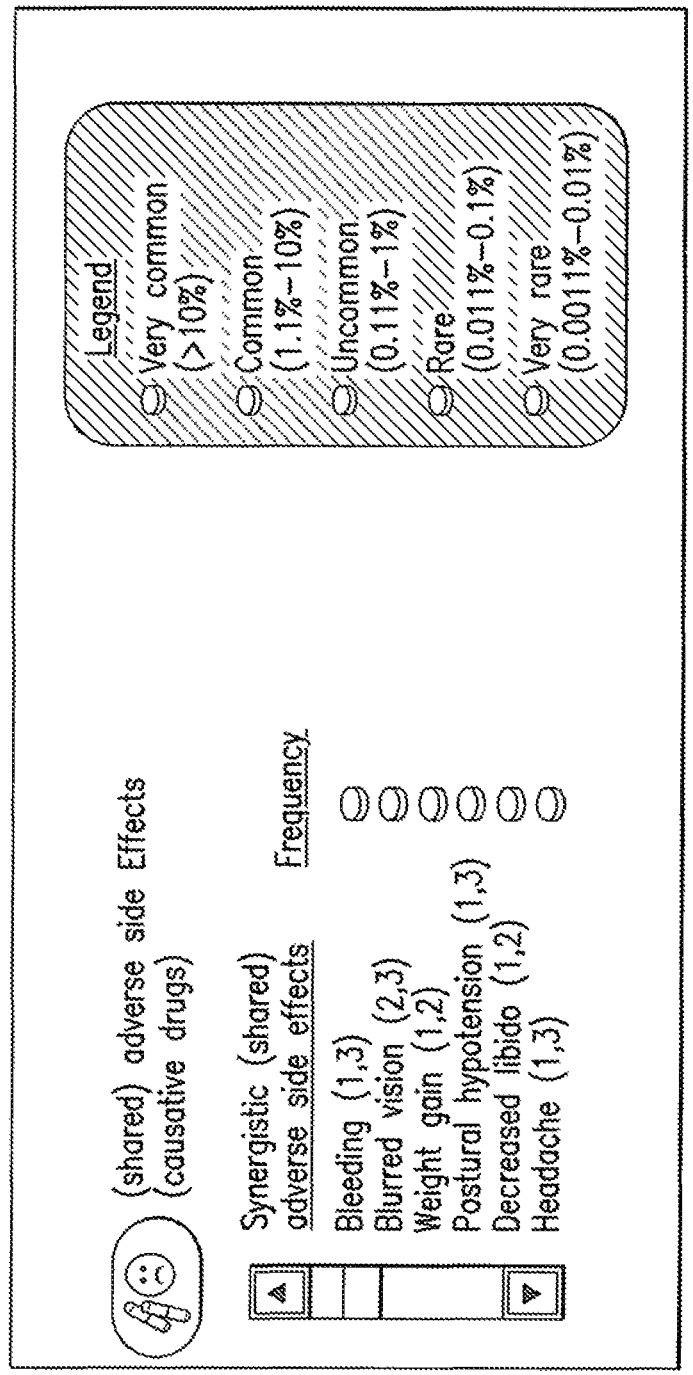
FIG. 10 is an exemplary screen capture from a GUI 180, according to an example embodiment of the present invention, showing shared adverse effects of more than two drugs in a patients cluster sharing common side effects, the number in brackets for each side effect indicating which drugs in the list share which effect.

One type of information that is noted and displayed in the main screen 190 and which is also used to define rules for generating alerts in example embodiments is shared side effects. In example embodiments, a Shared Adverse Side Effects Predictor 141 is included. The Shared Adverse Side Effects Predictor 141 notes possible side effects common to two or more of the drugs listed in the first column 210 of the main screen 190 and, to make the physician aware of cases where side effects are shared by more than one drug and require special attention or treatment as their shared effect may have a significant effect that would typically not be realized when considering side effects at the single drug level only; As shown in FIG. 5, this information may be clearly displayed to the physician (tab 350). See also FIG. 10. It will be appreciated that such information may also by used to configure rules by the Rules & Alert Engine 144 to trigger alerts.

HealthCare Burden Estimator 142

In some prior art database and prescription systems, the cost of drugs and of drug dosage regimes is available to the doctor, and can be used to apparently minimize costs to the Health Maintenance Organization (HMO). It should be appreciated, however, that the cost of the drug treatments is only a small fraction of the real Health Care Burden (HCB) which also includes hospitalization, visits to the Emergency Room (ER) and expensive imaging requirements.

In contradistinction to prior art approaches, examples of the present invention provide that drug treatment is correlated with overall healthcare events which themselves correlate with the patient's quality of life and costs/expenditures to the HMO. The overall healthcare events of interest include, inter alia, likelihood of hospitalization, duration of hospital stays, requirements for expensive diagnostics including but not limited to imaging techniques such as computed tomography (CT), Magnetic Resonance Imaging (MRI), Ultra Sound (US) and X-ray (XR), visits to the Emergency Room, visits to general practitioners (GPs) and/or specialized practitioners (SPs). Tis data may be collected together with details of drug clusters prescribed for a large sample of patients and may thereby provide an indication of the total likely cost of the drug prescription; not only the cost of the medication itself.

Such information is of interest to the treating physicians, patients as well as to government/Federal healthcare ministries HMOs and health insurers, as the true cost of treatment is heavily influenced by such correlations. Although the economic macro-effects of treatment regimes are examined for populations, it is suggested that these economic macro-effects are valuable indicators of the true health and well-being of the patient.

The actual cause of hospitalization may not be known but average costs are readily available. The HMO may also allow this data to be extracted from the EMR system for an average patient or for an average patient with similar profile.

It little matters if hospital admission is the result of the drugs ingested themselves, or of complex negative drug interactions, including accidents resulting from side effects such as dizziness of dehydration. Furthermore, it is immaterial if these interactions are properly diagnosed or not. Indeed, it little matters if lack of hospitalization is the result of more effective treatment of the symptoms, or even of a beneficial side effect where two drugs act symbiotically to create a feeling of wellbeing. The fact remains that a patient feeling better and not suffering from serious side effects will be less likely to be hospitalized or to require treatment in an emergency room (ER), or expensive imaging tests, etc. The lack of hospital and/or ambulatory based treatment is in the common interest of the patient, physician and of the HMO. Thus, it will be appreciated that economic data of interest to the HMO is also of interest to the patient.

Embodiments of the invention include a Health Care Burden Estimator 142 that estimates potential hospital events which may result from specific drug combinations. The healthcare burden is not merely the cost of the drugs themselves, but additional costs that have been found to be correlated, such as hospital admissions, numbers of days hospitalized, visits to ER and expensive diagnostic techniques such as imaging requirements that are symptomatic of overall healthcare. The present invention predicts these potential costs and uses the prediction as an indication of the effectiveness (success or failure) of a drug regimen. The approach favors preventative medicine, improves quality of life for the patient, minimizes costs to the HMO and provides a useful indication of the likely overall health effect on the patient to the doctor.

The Healthcare Burden Estimator 142 of the DDI+ Platform 140 may be configured using a look up table (LUT) maintaining cost-associated parameters that is updated periodically by or on behalf of the Health Maintenance Organization (HMO). Preferably, however, the Healthcare Burden Estimator 142 is correlated to records of the HMO to extract a statistically relevant prediction of the cost of the Health Care Burden based on treating similar patients.

Figure 11:
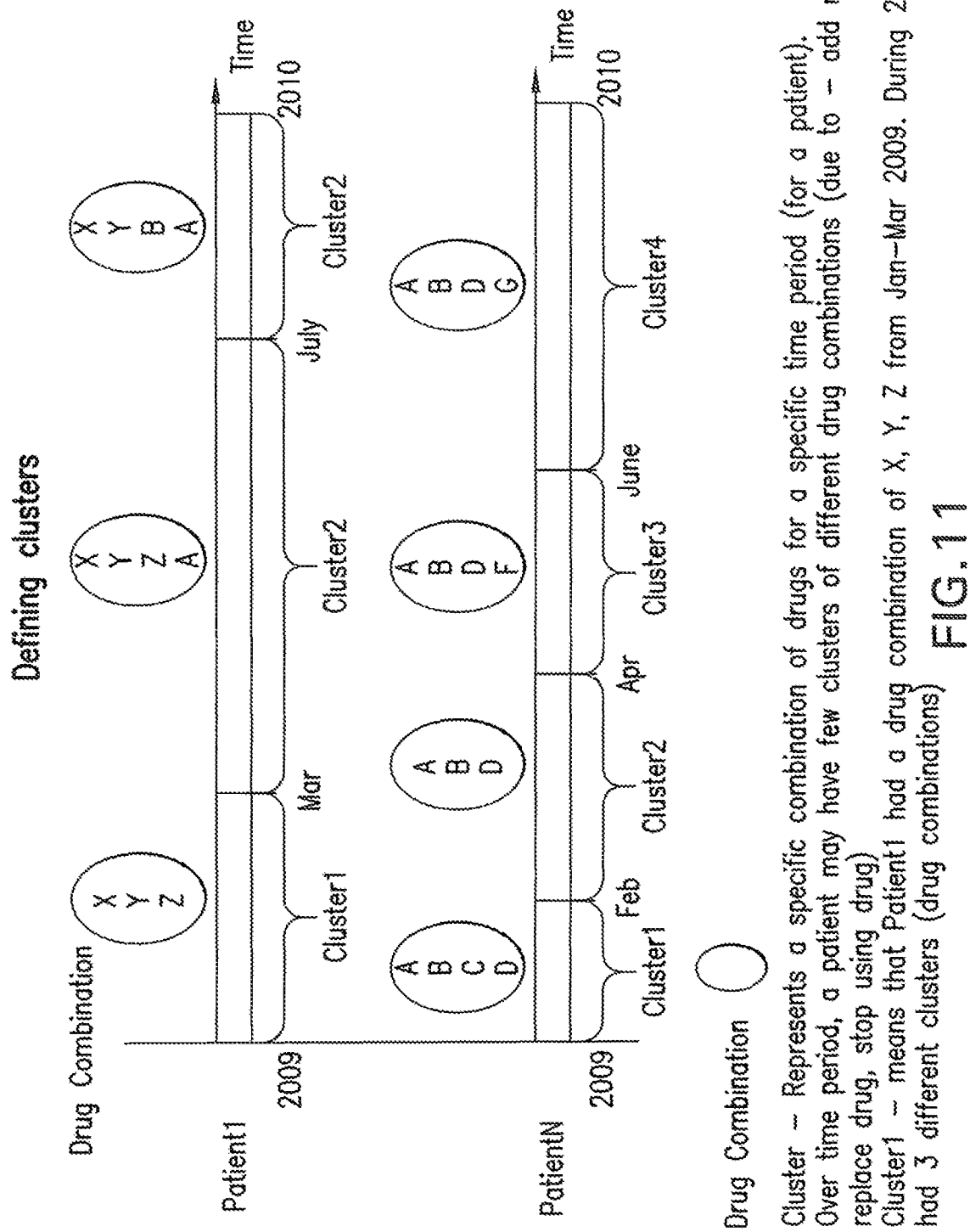
FIG. 11 shows how drug clusters may be defined for each patient, according to an example embodiment of the present invention.

FIG. 11 shows how, for each patient (1 to N), the various drugs taken in combination, considered herein as a drug cluster, may be tracked over time. In FIG. 11, each different drug is indicated by a capital letter.

FIG. 12 shows how the Healthcare Burden Estimator 142 processes and calculates the generated alerts for each cluster for each patient, by reference to information mined from the GENELEX™ 120 and FIRST DATABANK™ 130 databases.

Alternative Drug Suggester 143

The DDI+ platform 140 of the system 100 includes an alternative drug suggestor 143 that suggests proper and safe alternatives to the patient's drug regimen based on predicted drug-drug, drug-gene and metabolic-genetic profile related interactions.

Drug alternatives sorted by number of alerts (by criteria predefined by the user) will be presented to the physician Thus, inappropriate combinations will be screened out, enabling the physician to actively consider appropriate options only.

The alternatives are clearly labeled and are safe. In example embodiments of the present invention, the system considers and prepares a list of alternative drug options in an ongoing manner in the background, for display to the physician immediately when alternative options are demanded. In this manner, complex interactions and side effects are evaluated in the background and there is no significant delay waiting for the algorithms to generate and display results.

Figure 13:
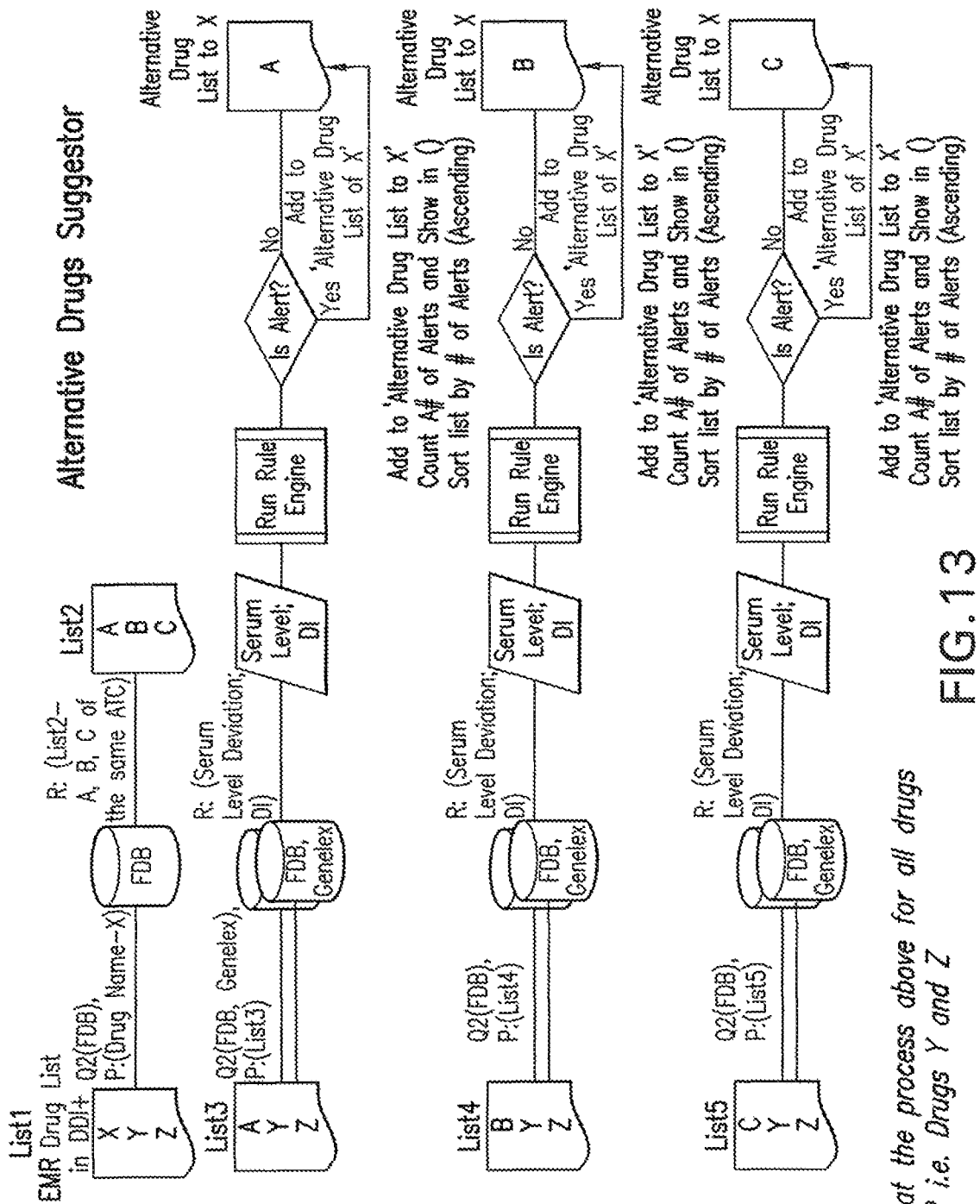
FIG. 13 is a schematic flowchart for an alternative drug suggester, according to an example embodiment of the present invention.

With reference to FIG. 13, essentially, the alternative drug suggestor 143 systematically substitutes candidate alternatives for specific prescribed drugs in turn, and extracts relevant data from the patient's history and from the databases 110, 120, 130. The DDI+ Platform 140 sorts the results by number of alerts that are generated for each drug, so that alternative drugs that do not generate more than a preset acceptable number of alerts (preferably none) are shown first to the physician to assure a safe alternative. The physician can, however, suggest a specific additional or alternative drug via the GUI 180 and see the potential effects thereof User Configurable Rules & Alerts Engine 144

Example embodiments of the present invention provide a Rules & Alerts Engine 144. An exemplary detail of the type of alerts provided is shown in FIG. 14. In example embodiments of the present invention, alerts are displayed to the physician. In example embodiments of the present invention, a powerful, flexible, rule based engine 144 is provided that enables the type and number of alerts displayed to be tailored to the HMO and the physician's judgment and specific needs as well as to the patient's specific scenario.

The alerts are in accordance with rules in the Rule & Alerts Module 144, some of which can be set by the doctor, so that only information of interest is displayed.

Current global clinical databases evaluate drug interactions based on their clinical outcome. Embodiments of the present invention additionally provide evaluation of economic outcome via the Health Care Burden Estimator 142. It will be appreciated that this is not merely a question of cost of drugs, but rather the total cost of treatment.

The Rules & Alerts Engine 144 allows user-configuration of rules in order to generate alerts; activation and deactivation of rules, defining whether rules will be applied to all the patients of a specific physician or to a specific patient; modification and customization of rules based on the inputs from databases including the patient's history from the electronic medical record database 110, serum level deviations from GENELEX™ database 120 and drug interactions from FIRST DATABANK™ database (FDB) 140, shared adverse side effects, healthcare burden that exceed preset values and other parameters derived from the processing performed by the DDI+ Platform 140 and from the databases.

In an example embodiment of the present invention, the Rules & Alert Engine 144 supports a hierarchical arrangement of privileges. Some rules and threshold values are set by the service provider and cannot be over-ridden by the user. A lower level of rules and/or threshold values may be set by the service provider or the HMO and can be over-ridden. In example embodiments, the physician will be able to set some rules in accordance with personal preferences. In some embodiments, changing rules or resetting threshold values will be according to user's permission levels (e.g., determined by passwords, magnetic swipe carts, biometric identification and the like).

Preferably the rules of the Rules & Alert Engine 144 and their hierarchical arrangement use operands available in a list, perhaps from a drop down menu, so that the programmer or user can configure the system using common symbols such as "< >+–=" and the like.

In an example embodiment, at least at an administrator level, complex rules can be configured using a plurality of conditions (AND, OR), and severities. For example, the type of rules for a combination of conditions and or severities that may be supported might include:
1. If Increased Serum Level deviation>70 AND NTI (Narrow Therapeutic index)=Yes then generate Alert.
2. For HCB calculation—If there is [1 Severe value AND 2 Moderate AND 2 Serum Deviations>50%] then generate Alert.
3. If Side Effect (Select specific Side Effect from list), e.g., 'Side Effect'="Bleeding," and 'Frequency'="More Frequent" and 'Severity'="Severe," then generate Alert
4. If Side Effect (Any side effect), e.g., 'Side Effect'="All," and 'Frequency'="More Frequent" and 'Severity'="Severe," then generate Alert.

Example embodiments support user-configurable rules based on information provided by proprietary tools such as the Shared Adverse Side Effects Predictor 141, the HCB Estimator 142 as well as on patient factors such as gender, race and genetics, sensitivities, smoking, alcohol and pregnancy, in addition to alerting on drug-drug interactions and potential deviations from serum levels using data provided by commercially available tools, such as the GENELEX™ database 120 and the FIRST DATABANK™ database 130. In some embodiments, these rules are switched ON and OFF in accordance with the patient's medical record EMR. In other embodiments, these rules are set to defaults that, to prevent the user being flooded with alerts, are typically switched OFF but may be switched ON or OFF.

There are different kinds of rules and alerts which different level users can add or cancel. High level alerts may be built into the Rules & Alert Engine 144 of the DDI+ platform 140 and cannot be over-ruled or switched OFF and will always be displayed to the treating physician or other user, whereas lower level alerts may be set by the user for all patients, a group of patients, such as geriatrics, those treated within a particular framework, those hospitalized, etc, or for individual patients considered individually. Although the physician may not be able to switch off some alerts and can prevent others from being displayed, the alerts are provided for display in the GUI 180 of the DDI+ platform 140 and have no direct effect on what drugs the physician may or may not prescribe.

In an example, the Rules & Alert Engine 144 may be a learning platform that takes into account the physician's remarks as input into the system and empirical evidence for the patient collected over time as part of the patient's personal medical history, to adjust the number and types of alerts provided. In embodiments, the physician may overrule alerts and may configure the rules of the alert-based engine 144 of the DDI+140 to display alerts of specific types or not to display them. The overrides are logged/documented for monitoring by the physician and/or management and the report generator 145 provides such information, which is an indication of the quality of the treatment.

One particular type of alert supported by the Rules & Alerts Engine 144 is an alert of the Health Care Burden (HCB) of a particular combination of drugs. This alert uses information extracted by the health care estimator 142. In addition to helping generate and display alerts, the Health Care Burden estimator 142 calculates and presents the contribution of some or each (e.g., the main) drug at the drug level to the Health Care Burden score so that physician can take it into consideration.

FIG. 14 shows a table of alerts according to an example embodiment of the present invention. By providing a system of alerts it is possible to tweak treatment to make alerts go away. In example embodiments, the physician can overrule alerts or prevent them being displayed due to knowledge of the patient's case and specific needs. Nevertheless, a system of alerts, which may be set by the Health Maintenance Organization (HMO), the general practitioner or specialist doctor, and which includes patient's factors and estimates from the Health Care Burden Estimator, would statistically improve the quality of the treatment by reducing required hospital treatment.

Thus, the DDI+ 140 in general and the alerts generated thereby, are tools that provide information to the physician, and facilitate better decision making, more effective prescription and better treatment, but are in no way limiting on the physicians freedom to treat his or her patients.

The Reporter Generator 145

The Reporter Generator 145 generates reports concerning the physician's usage of the DDI+ Platform 140 and other statistics, efficiency parameters, etc. Such reports may be of interest to various parties such as the product developers, the HMO, the physician, the patient, academic researchers and the like.

Statistical Module 146

The statistical module 146 may collect and aggregate statistical information, including logs and poly-pharmaceutical alerts relating to the patient's drug cluster level, and may, using associated analysis software, enable statistical analysis at various scales, such as for all patients of a number of HMOs, the patients of a specific HMO, hospital, or clinic, the patients of a specific physician and/or the individual patient. The statistical information may be used by the various tools of the system such as the reporter 145, the HCB Estimator 144, the Rules & Alert Engine, etc.

For example the statistical module 146 may be configured to track the physician's success in overcoming alerts over a time period by prescribing alternative treatments.

Method of Operation

Figure 15:
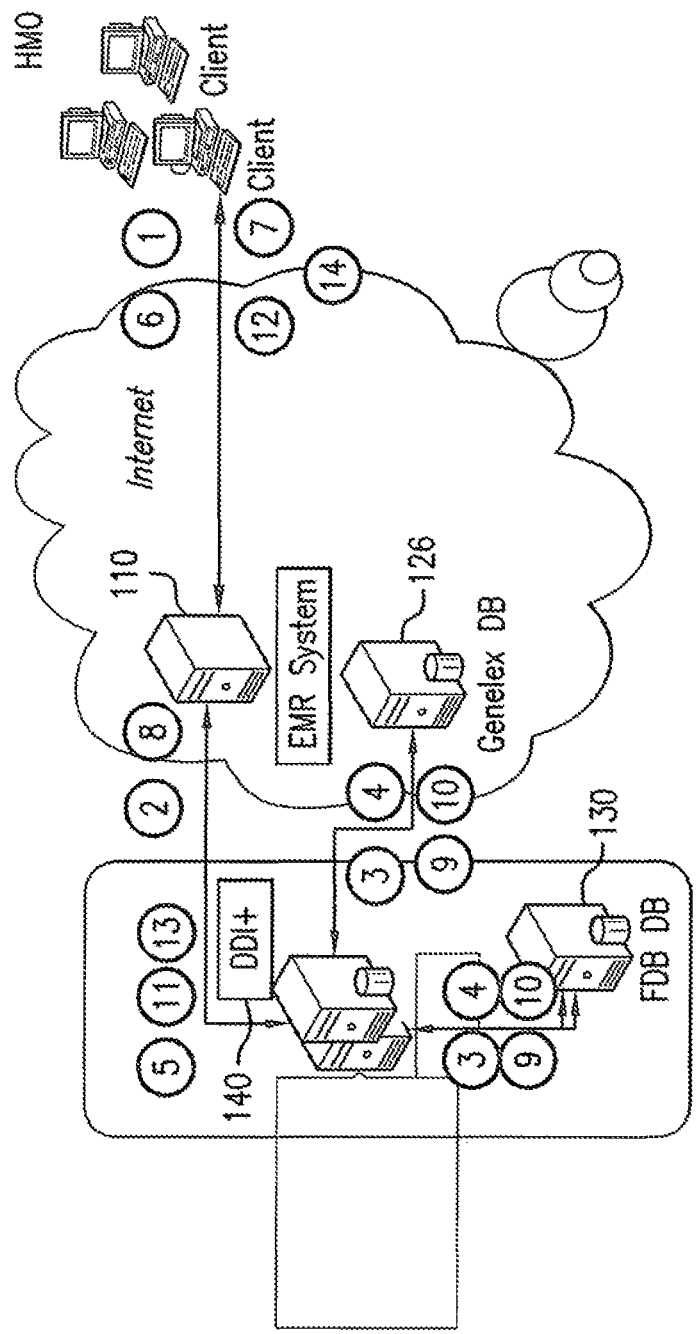
FIG. 15 is an example workflow in accordance with an example embodiment of the invention.

The above description describes the features and the functional elements of the system, which includes commercially available databases and tools and the proprietary DDI+ Platform 140. With reference to FIG. 15, in an example embodiment of the present invention, the DDI+ Platform 140 integrates and synchronizes data from various databases. In the current embodiment shown, these include the GENELEX™ database 120, which primarily provides information about serum level deviations and genetic information, and the FIRST DATABANK™ (FDB) 130 which provides information results regarding drug-drug interactions, side effects and the like.

In an integrated mode, the DDI+ Platform 140 is integrated with the Electronic Medical Record (BMR) of the patient from the EMR database 110 held by the Health Maintenance Organization (HMO). In other modes, this may be freestanding.

An icon for the DDI+ Platform 140 appears in the electronic medical record (EMR) with a color coding that indicates status, typically Green indicating No Alerts, and Red indicating that Alerts were generated. (The icon for the DDI+ could be configured to itself change color or an indicator light can be displayed alongside).

When a user, typically the physician, enters a specific patient's EMR, such as by passing the patient's magnetic card (1) or by entering the national insurance or identity number of the patient, the EMR system 110 triggers the DDI+ Platform 140 with the following information:

Encoded Doctor ID
Patient ID
Patient's drug regimen (i.e., the list of drugs consumed by the patient, Drug Cluster)
Additional patient factors if within the EMR, such as Genetics, Age, Gender, Pregnancy, etc. (2).

The DDI+ Platform 140 then starts its processing in the background, not interfering with the user's routine work of patient treatment and prescription.

The DDI+ Platform 140 queries the FDB database 130 which in the embodiment illustrated is maintained locally, but in other embodiments may be accessed remotely, with details of the drug cluster to obtain results concerning potential interactions, side effects, etc, for the drug specific cluster. The DDI+ Platform 140 also runs the Alternative Drug Suggestor 143 in the background in order to prepare in advance the list of proper alternative drugs for each drug in the patients drug cluster (3).

Additionally, the DDI+ Platform 140 queries the GENELEX™ Database 120 using GENELEX™ API with the Drug Cluster in order to get results about potential serum level deviations for the specific drug cluster.

The DDI+ Platform 140 runs the Alternative Drug Suggestor 143 in order to prepare in advance a list of proper alternative drugs for each drug in the patient's drug cluster.

Upon receipt of the results from GENELEX™ 120 and FDB 130 (4), the DDI+ Platform 140 runs the Shared Adverse Side Effect Module (SASE) 141, the HealthCare Burden Estimator (HCB) 142 and the Rule & Alert Engine 144 with pre-defined user configurable rules that are variously definable by the HMO and/or user as most critical to trigger Alerts, and checks for and displays Alerts triggered thereby.

In case of a violation of any of the pre-defined rules, the DDI+ Platform 140 generates an alert. In an example, the results of the Shared Adverse Side Effect Module 141 and the HealthCare Burden Mechanism 142 may be also used as input for setting user-configurable rules.

The DDI+ Platform 140 then triggers the EMR system with a status indication concerning whether Alerts have been generated or not (5). If Alerts have been generated, the EMR system changes the DDI+ icon in the main screen of the EMR to Red in order to indicate to the user that Alerts have been generated and require his/her attention (6). The user can then access the web-based GUI 180 of the DDI+ Platform 140 in order to explore the reasons for the generated alert(s). The results and the alerts are displayed to the user immediately, via the main screen 190 of the GUI 180 (FIG. 5) in an intuitive, comprehensive and user-friendly manner, thereby doing away with the need to navigate between multiple screens and irrelevant information. As shown in FIG. 5, the main screen 190 of the GUI 180 of the DDI+ Platform 140 is configured to allow the user to intuitively drill down to access further details for further analysis such as drug monographs, details of the interactions, relevant references, side effects, shared adverse side effects and the like.

The user may decide to look for an alternative drug to a specific drug previously prescribed, based on the alerts provided by the system. Because DDI+ 140 runs in the background before the GUI 180 is even opened, the alternative drugs for each drug prescribed are already prepared and checked by DDI+ 140 to ensure that no more than an acceptable number of alerts are generated in cases where the specific alternative drug is chosen, thus ensuring safe treatment for the patient and minimizing the time required by the user to access the desired information. In examples, only alternatives generating fewer alerts than the number generated by the drug it is replacing within the current drug regimen am suggested. In one example embodiment, for most patients and in most scenarios, no alerts are acceptable (i.e., if any alert is triggered, the system does not output the possibility of the drug's use as an alternative).

Furthermore, the DDI+ Platform 140 runs the Shared Adverse Side Effects (SASE) Predictor 141 that enables detection and user-configurable alerting upon side effects having pre-defined frequencies and severities that are shared by two or more drugs in the patient's drug combination (Shared Adverse Side Effects) (7).

Upon any change in the patient EMR, such as prescription of a new drug, replacing a drug or stopping a drug, the DDI+ Platform 140 is triggered again by the EMR and the above described workflow takes place (8, 9, 10, 11, 12). The DDI+140 again checks for Alerts 210 and runs the relevant processes including the Shared Adverse Side Effects Predictor 141, the HCB Estimator 142 and the Rule & Alert Engine 144, on the updated patient's drug cluster.

The user may also use the DDI+ Platform 140 for simulation purposes by accessing it directly and not via the EMR, and can perform a variety of actions such as Add, Delete, Replace drug and the like, to obtain relevant data from the DDI+ Platform 140 before making any changes within the EMR (13, 14).

Figure 16:
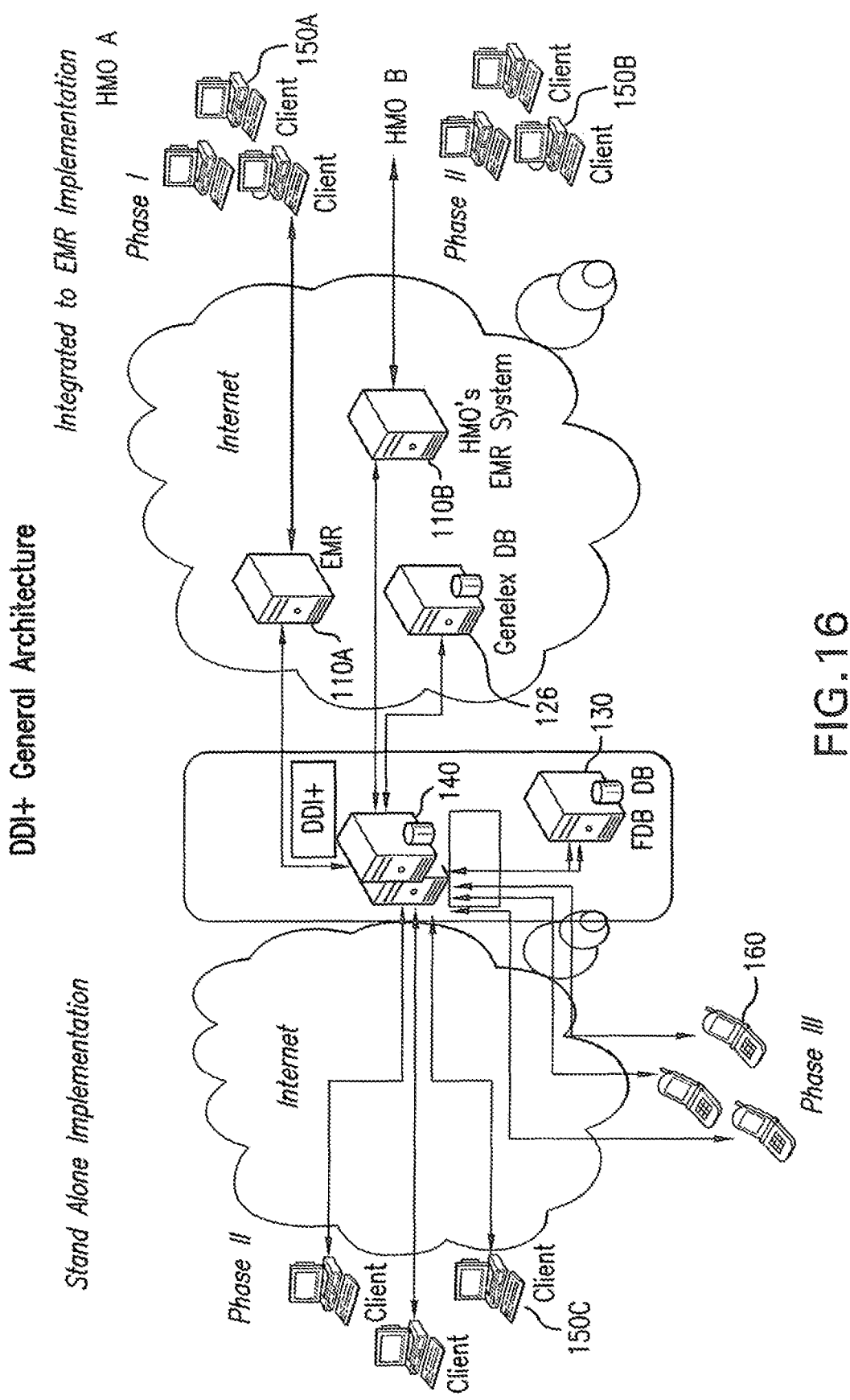
FIG. 16 shows alternative configurations of a system for access by multiple HMOS and directly by physicians in a stand-alone mode, using a web browser, such as via computers, a mobile phones, a tablets and the like, according to an example embodiment of the present invention.

With reference to FIG. 16, in example embodiments, the DDI+140 may interact with the clients 150A, 150B of more than one HMO, via the EMR Databases thereof 11A, 110B, making GENELEX™ 120, and FDB 130 available to more than one HMO. The DDI+ may also be directly accessed over the Internet, via a client terminal 150C, a freestanding PC, or via a mobile phone 160.

CONCLUDING REMARKS

Thus, example embodiments of the present invention include the following features of interest:

The platform is either a stand-alone web platform or integrated with HMO's Patients EMR.

A personalized solution based on the patient's EMR and genetic profile is offered.

The system comprehensively, amalgamates clinical, genetic and metabolic data.

Drug-drug interactions are indicated, preferably for any two combinations of drugs and most preferably for the multiple interactions of more than two drugs. Gene-drug interactions for the patient are predicted and displayed. The interactions indicated include, among others, side-effects, reductions in efficacy including non-responsiveness and toxicity.

The platform may be self educating. It incorporates physicians comments and applies them thereafter.

Alerts may be provided based on pre-defined rules set by the user/IMO. The alerts generated can cover all aspects of both data extracted by the DDI+ Platform from commercially available tools and databases as well as data outputs processed by proprietary tools of the DDI+ Platform.

Alerts generated relate to shared side effects, potential deviation of drugs from their expected serum levels, contra-indications and the overall Healthcare Burden.

A unique alternative drugs suggestion mechanism may suggest alternative drugs to patients' regimens. A uniqueness of this mechanism is that it screens a plurality of potential alternative drugs and lists them to the user/HMO while showing if such alternatives exert any user-predefined alerts.

The user can select and prescribe an alternative drug while knowing, in advance, that it will or will not generate any activated alerts in the system when combined with other drugs in the patients' current drug-regimen.

The potential costs of patients' treatment due to the drug cluster considered, mainly potential indirect costs related to increased referrals to emergency rooms, increased hospitalization rates & duration, increased referrals to imaging procedures (CT, MRI, US, RX etc.) are presented to the user/HMO and by that enables to shift patients from a current drug regimen which might greatly increase the healthcare burden associated with the patient to an alternative and preferable drug combination which is predicted to decrease the usage and costs of such healthcare resources.

The system is web based and can be accessed by relevant parties such as physicians using any web browsers, including mobile and desktop computers, tablets, mobile phones, i-pads, i-phones and the like.

An intuitive GUI is provided to help navigate the information available in an efficient manner.

It will be seen, therefore, that the method and system described hemin will facilitate improved treatment regimes and higher quality of life for patients. By minimizing the necessity of expensive treatments, it will enable resources to be better used and have a further knock on effect to other patients.

Although GENELEX™ 120 and FIRST DATABANK™ (FDB) 130 are given as databases of information regarding drug interactions and serum levels respectively, it will be appreciated that other commercially available or proprietary databases may be added or substituted.

In an example embodiment, data relating to drug effects on serum levels, genetic and racial effects on drugs, patient sex, age and weight, and literature information am all used in optimizing the prescribing of drugs to the patient. Simpler systems missing any or all of the above considerations can, nevertheless also be used.

An example embodiment of the present invention is directed to one or more processors, which may be implemented using any conventional processing circuit and device or combination thereof e.g., a Central Processing Unit (CPU) of a Personal Computer (PC) or other workstation processor, to execute code provided, e.g., on a hardware computer-readable medium including any conventional memory device, to perform any of the methods described herein and/or to provide any of the user interface functionality described herein, alone or in combination. The one or more processors may be embodied in a server or user terminal or combination thereof. The user terminal may be embodied, for example, as a desktop, laptop, hand-held device, Personal Digital Assistant (PDA), television set-top Internet appliance, mobile telephone, smart phone, etc., or as a combination of one or more thereof. The memory device may include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to one or more hardware-implemented computer readable media, e.g., as described above, having stored thereon instructions executable by a processor, which, when executed, cause one or more processors to perform the example methods described above, or portions thereof, for example, to provide the user interface functionality and/or make the various therapy determinations described herein.

An example embodiment of the present invention is directed to a method of transmitting instructions executable by one or more processors, the instructions, when executed, causing the processor(s) to perform the example methods described above, or portions thereof.

Features shown with some specific embodiments may be incorporated with other embodiments. Preferred embodiments are described, and simpler embodiments and alternatives may be within the scope of the invention. Thus, the scope of the present invention encompasses the embodiments described above, each alone or in combination, and includes both combinations and sub combinations of the various features described hereinabove as well as variations and modifications thereof, which would occur to persons skilled in the art upon reading the foregoing description.

What is claimed is:

1. A method comprising:
   utilizing, by a predictive computing platform, a plurality of Application Programming Interfaces (APIs) to obtain, over a computer network in real time, a plurality of data-sets from a plurality of disparate data sources, wherein the plurality of data-sets comprises patient-related data in a plurality of distinct data formats;

integrating, by the predictive computing platform, the plurality of patient-related data sets into an integrated patient-related data set;

transforming, by the predictive computing platform, a data-set of drug-related adverse reaction alerts to a reduced patient-specific data-subset of drug-related adverse reaction alerts by utilizing the integrated patient-related data set and a decision algorithm, wherein the utilizing of the decision algorithm comprises, for each drug-related adverse reaction alert of the data-set of drug-related adverse reaction alerts:

i) determining whether a patient is:
1) at an elevated risk to experience a particular drug-related adverse reaction; or
2) not at the elevated risk to experience the particular drug-related adverse reaction,
wherein the determining is based on:
a) current drug intake data,
b) candidate drug intake data,
c) a plurality of patient specific parameters,
d) drug-related adverse reaction data from the data-set of drug-related adverse reaction alerts, and
e) at least one pre-determined severity level for at least one of:
I) a drug-drug interaction ("DDI"),
II) a drug-patient interaction ("DPI"),
III) a drug-food interaction ("DFI"), or
IV) any combination thereof;
ii) including, into the reduced patient-specific data-subset of drug-related adverse reaction alerts, each drug-related adverse reaction alert where the patient is at the elevated risk; and
iii) removing, from the data-set of drug-related adverse events, each drug-related adverse reaction alert where the patient is not at the elevated risk; and
causing, by the predictive computing platform, to output, over the computer network in real time, the reduced patient-specific data-subset of drug-related adverse reaction alerts to a graphical user interface on a screen of a computing device.

2. The method of claim 1, wherein the plurality of disparate data sources is chosen from at least two of: a source of genetic data, electronic medical records, a database of pharmaceutical drugs, a database of nutraceuticals, a database of herbal remedies, a database of dietary supplements, or any combination thereof.

3. The method of claim 2, wherein the source of genetic data is a source of genetic test data.

4. The method of claim 2, wherein the database of pharmaceutical drugs is a database of prescription pharmaceutical drugs.

5. The method of claim 2, wherein the database of pharmaceutical drugs is a database of over-the-counter (OTC) pharmaceutical drugs.

6. A predictive computing platform comprising:
at least one processor, and
a non-transitory computer memory, storing a computer program that, when executed by the at least one processor, causes the at least one processor to:
utilize, by a predictive computing platform, a plurality of Application Programming Interfaces (APIs) to obtain, over a computer network in real time, a plurality of data-sets from a plurality of disparate data sources,
wherein the plurality of data-sets comprises patient-related data in a plurality of distinct data formats;
integrate, by the predictive computing platform, the plurality of patient-related data sets into an integrated patient-related data set;
transform, by the predictive computing platform, a data-set of drug-related adverse reaction alerts to a reduced patient-specific data-subset of drug-related adverse reaction alerts by utilizing the integrated patient-related data set and a decision algorithm,
wherein the utilizing of the decision algorithm comprises, for each drug-related adverse reaction alert of the data-set of drug-related adverse reaction alerts:
i) determining whether a patient is:
1) at an elevated risk to experience a particular drug-related adverse reaction; or
2) not at the elevated risk to experience the particular drug-related adverse reaction,
wherein the determining is based on:
a) current drug intake data,
b) candidate drug intake data,
c) a plurality of patient specific parameters,
d) drug-related adverse reaction data from the data-set of drug-related adverse reaction alerts, and
e) at least one pre-determined severity level for at least one of:
I) a drug-drug interaction ("DDI"),
II) a drug-patient interaction ("DPI"),
III) a drug-food interaction ("DFI"), or
IV) any combination thereof;
ii) including, into the reduced patient-specific data-subset of drug-related adverse reaction alerts, each drug-related adverse reaction alert where the patient is at the elevated risk; and
iii) removing, from the data-set of drug-related adverse events, each drug-related adverse reaction alert where the patient is not at the elevated risk; and
cause, by the predictive computing platform, to output, over the computer network in real time, the reduced patient-specific data-subset of drug-related adverse reaction alerts to a graphical user interface on a screen of a computing device.

7. The system of claim 6, wherein the plurality of disparate data sources is chosen from at least two of: a source of genetic data, electronic medical records, a database of pharmaceutical drugs, a database of nutraceuticals, a database of herbal remedies, a database of dietary supplements, or any combination thereof.

8. The system of claim 7, wherein the source of genetic data is a source of genetic test data.

9. The system of claim 7, wherein the database of pharmaceutical drugs is a database of prescription pharmaceutical drugs.

10. The system of claim 7, wherein the database of pharmaceutical drugs is a database of over-the-counter (OTC) pharmaceutical drugs.

* * * * *